(12) United States Patent
Srivastava et al.

(10) Patent No.: US 8,981,076 B2
(45) Date of Patent: Mar. 17, 2015

(54) SYNTHESIS OF N-FMOC PROTECTED DEOXY NUCLEOSIDES, RIBO NUCLEOSIDES, MODIFIED DEOXY AND RIBO NUCLEOSIDES, AND PHOSPHORAMIDITES, AND THEIR USE IN OLIGONUCLEOTIDE SYNTHESIS

(75) Inventors: Suresh C. Srivastava, Burlington, MA (US); Naveen P. Srivastava, Burlington, MA (US)

(73) Assignee: ChemGenes Corporation, Wilmington, MA (US)

( * ) Notice: Subject to any disclaimer, the term of this patent is extended or adjusted under 35 U.S.C. 154(b) by 617 days.

(21) Appl. No.: 12/592,680

(22) Filed: Nov. 30, 2009

(65) Prior Publication Data

US 2011/0015382 A1    Jan. 20, 2011

Related U.S. Application Data

(60) Provisional application No. 61/200,592, filed on Nov. 29, 2009.

(51) Int. Cl.
*C07H 21/00* (2006.01)
*C07H 19/073* (2006.01)
*C07H 19/173* (2006.01)

(52) U.S. Cl.
CPC ............ *C07H 19/073* (2013.01); *C07H 19/173* (2013.01)
USPC ...................................... 536/25.31; 536/25.3

(58) Field of Classification Search
None
See application file for complete search history.

(56) References Cited

PUBLICATIONS

Wilds et al. Nucleic Acids Research (2000), vol. 28, pp. 3625-3635.*
Heikkila et al. Acta Chemica Scandinavica (1983), vol. 37, pp. 263-265.*

* cited by examiner

*Primary Examiner* — Patrick Lewis
(74) *Attorney, Agent, or Firm* — Law Offices of Indu M. Anand; Indu M. Anand, Esq.

(57) ABSTRACT

This invention relates to synthesis of novel -N-FMOC protected nucleosides, succinates, phosphoramidites, corresponding solid supports that are suitable for oligo deoxy nucleosides and RNA oligonucleotide synthesis. Our discovery using N-FMOC as nucleoside base protecting group, which is highly base labile protecting group is a novel approach to obtain highest purity oligonucleotides. This approach is designed to lead to very high purity and very clean oligonucleotide, after efficient removal of the protecting groups and to produce high purity therapeutic grade DNA oligonucleotides, RNA oligonucleotides, diagnostic DNA, diagnostic RNA for microarray platform. The deprotection of FMOC protecting groups of the natural deoxy and ribonucleosides occurs under very mild deprotection conditions such as mild bases, secondary and tertiary amines for removal of such groups under such conditions would allows synthesis of various DNA and RNA of highest purity for diagnostics and therapeutic application. This approach is further designed to use FMOC protecting group on various base sensitive nucleoside, and for use in oligo peptide synthesis and for support bound oligo nucleotides. DNA oligonucleotides containing 3'-end dA at the 3'-terminal will be produced using the FMOC-dA-supports would lead to much reduced M−1 deletion sequences, and thereby high purity.

3 Claims, 17 Drawing Sheets

Fig 9.A

Batch : NS226-18.sre

| | A | B | C | D | E | F | G | H |
|---|---|---|---|---|---|---|---|---|
| 1 | NS226-18 | | 1 | 2 | 3 | 4.0 | 5.0 | Emax |
| 2 | Cycle01 | nm | 250.0 | 260.0 | 280.0 | 250/260 | 260/280 | 260.0 |
| 3 | Manual | A | 1.324 | 1.422 | 0.967 | 0.931 | 1.470 | 33118 |
| 4 | Cycle02 | nm | 250.0 | 260.0 | 280.0 | | | |
| 5 | Manual | A | 1.322 | 1.417 | 0.966 | 0.933 | 1.467 | 32862 |
| 6 | Cycle03 | nm | 250.0 | 260.0 | 280.0 | | | |
| 7 | Manual | A | 1.316 | 1.411 | 0.965 | 0.933 | 1.461 | 33002 |
| 8 | Ave. Value | | | | | 0.933 | 1.466 | 32994 |

SYNTHESIS OF N-FMOC PROTECTED DEOXY NUCLEOSIDES, RIBO NUCLEOSIDES, MODIFIED DEOXY AND RIBO NUCLEOSIDES, AND PHOSPHORAMIDITES, AND THEIR USE IN OLIGONUCLEOTIDE SYNTHESIS

CROSS REFERENCE TO RELATED APPLICATIONS

This application claims priority from U.S. application Ser. No. 61/200,592, filed on Nov. 29, 2008. The entire contents of the prior application are herein incorporated by reference.

TECHNICAL FIELD OF THE INVENTION

This invention relates to the synthesis of novel 9-fluorenylmethyloxycarbonyl (N-FMOC) protected nucleosides, succinates, phosphoramidites, and corresponding solid supports, which are suitable for oligo deoxy nucleosides and RNA oligonucleotide synthesis. The use of N-FMOC as nucleoside base protecting group, which is highly base labile protecting group, is a novel approach to obtain highest purity oligonucleotides.

BACKGROUND ART

It is known that the chemical synthesis of oligonucleotides of DNA fragments is performed efficiently by the phosphoramidite chemistry, and the coupling reaction gives excellent yield on various solid supports (Oligodeoxy nucleotide synthesis, Phosphoramidite Approach, Serge L. Beaucage in Protocols For Oligonucleotide s and Analogs, Synthesis and Properties, Editor, Sudhir Agarwal, Humana Press, 1993). Similarly, excellent protocols have been developed for the synthesis of RNA, and various biologically active tRNA molecules (Oligoribonucleotide synthesis, The Silyl Phosphoramidite Method, Masad J. Damha and Kevin K. Ogilvie in Protocols For Oligonucleotides and Analogs, Synthesis and Properties, Editor, Sudhir Agarwal, Humana Press, 1993).

A large number of such DNA and RNA molecules with biological functionality carry base labile and modified nucleosides which cannot sustain prolonged basic conditions, generally required during deprotection. Thus, e.g., dihydrouridine present in tRNA requires very mild deprotection conditions, otherwise it is completely decomposed and the quality of synthetic tRNA is compromised. (C. Chaix, D. Molko and R. Teoule, Tetrahedron Letters, 30, 1, 711-74, 1989).

In order to develop protecting groups which are ultra mild in nature have been developed in recent past. Thus 2-(acetoxy-methyl)benzoyl (AMB) group which uses potassium carbonate as mild deprotecting group for their removal has been reported (W. H. A. Kuijpers, J. Huskens and C. A. A. Van Boeckel, Tetrahedron Lett., 31, 6729-6732, 1990) & W. H. A. Kuijpers, E. Kuyl-Yeheskiely, J. H. Van Boom and C. A. A. Van Boeckel, Nucl. Acids Res., 21, 3493-3500, 1993). The AMB group seems attractive, but faces many practical problems in actual use. Although FMOC group has been reported in the prior art for the protection of amino function of 2'-deoxycytidine, 2'-deoxy adenosine and 2'-deoxy guanosine and for the corresponding ribonucleosides (H. Heikkila and J. Chattopadhyaya, Acta Chem. Scand. B 37, No. 3, 263-265, 1983), it has attractive properties as n-protecting group; as pointed out by these authors, the FMOC group offers the capability to be cleaved under very mild alkaline deprotection condition, or by bases capable to carry out selective deprotection via B-elimination of FMOC group (scheme 1).

It is therefore not surprising that other attempts to synthesize N-FMOC protected nucleoside and phosphoramidites have been carried out. Reported in the literature (R. K. Gaur, V. Bobde, M. Atreyi and K. C. Gupta, Indian Journal of Chemistry, 29B, 108-112, 1990), is the preparation of 5'-DMT-n-FMOC-dA (structure 1) and 5'-DMT-n-FMOC-dC (structure 2).

However this team could not synthesize 5'-DMT-N-FMOC-dG (Structure 5). Furthermore, they only synthesized p-methoxy phosphoramidites of 5'-DMT-n-FMOC-dC (structure 3) and 5'-DMT-n-FMOC dA (structure 4), and p-methoxy phosphoramidites have been found to have only limited application in oligonucleotide synthesis.

Also, no N-FMOC protected solid supports were reported by this team.

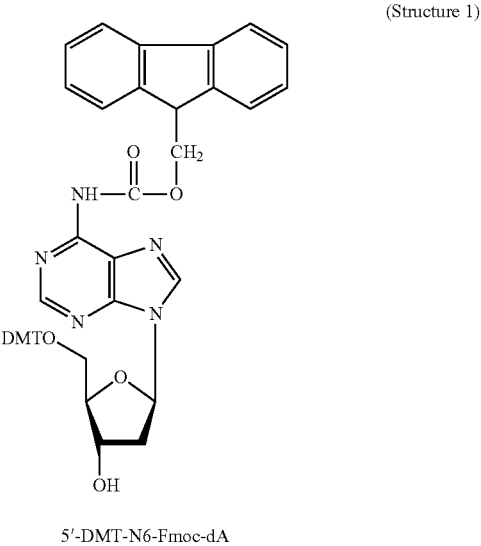

5'-DMT-N6-Fmoc-dA (Structure 1)

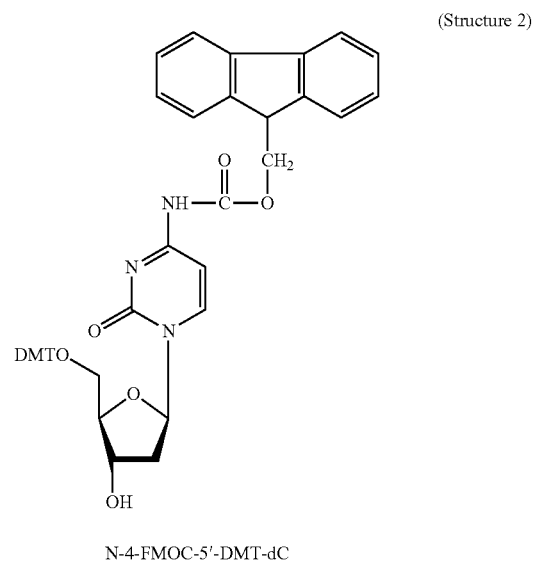

N-4-FMOC-5'-DMT-dC (Structure 2)

(Structure 3)

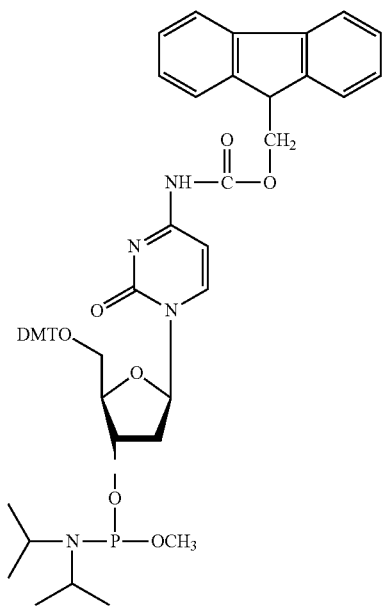

5'-DMT-N4-Fmoc-dC-
p-methoxy-phosphoramidite (Structure 4)

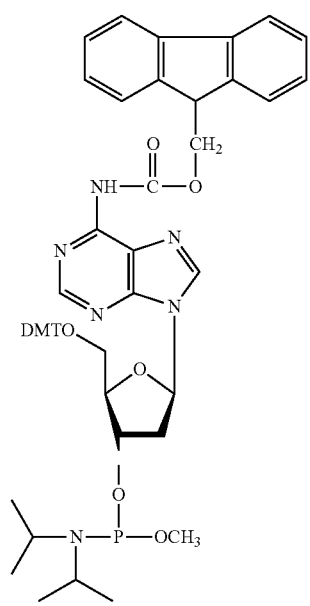

N-6-FMOC-5'-DMT-dA-
p-methoxy-phoshoramidite (structure 5)

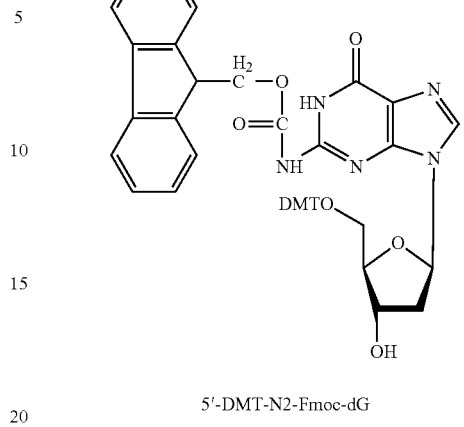

5'-DMT-N2-Fmoc-dG

The synthesis of N2-FMOC-5'-DMT-dG (structure 5) has eluded the researchers so far. In addition, no solid supports or the succinates of the N-FMOC-5'-DMT-deoxy bases (dA ad dC) are revealed by these authors. Thus, there is no information in this prior art as to the applicability of DMT-N-6-FMOC-dA-3'-succinyl-support, to validate the concept that the solid support containing N-6-Fmoc-dA solid supports is expected to minimize or dramatically reduce formation of N-1 (i.e. depurination of 3'-dA base products) during oligo synthesis, nor is there information about the quality of the synthesized 2'-deoxy oligonucleotides. The products are therefore required to improve the quality of the terminal 3'-dA containing oligonucleotides.

There seem to have been no further attempts to make 5'-DMT-N-FMOC dG or the ribonucleoside containing N-Fmoc protected synthons for RNA synthesis and the corresponding cyanoethyl phosphoramidites. The present state of the art in this technology relies on cyanoethyl phosphoramidite chemistry in DNA and RNA synthesis.

It was demonstrated by Heikkila and Chattopadhyaya, (Acta Chem. Scand. B 37, No. 3, 263-265, 1983) that deprotection of FMOC protecting group can be carried out under various very mild basic reaction conditions. It is possible to utilize either aq ammonia condition deprotection, which results in nucleophilic displacement of FMOC protecting group, or by a non-nucleophilic base such as triethylamine, which causes B-elimination of FMOC-active hydrogen group (scheme 1).

The FMOC protecting group is very well established in peptide synthesis and one of the preferred reagent for amino group protection of alpha-amino group of amino acids for step wise peptide synthesis (Carpino, L. A., and Han, G. Y., J. Amer. Chem. Soc., 92, 5748, 1970). However, despite the promise of the FMOC group, Heikkila and Chattopadhyaya, who initiated the synthesis of the FMOC deoxy and ribo nucleosides, themselves switched to another N-protecting group, i.e., 2-nitrophenyl sulfenyl (Nps) for the protection of amino function of cytidine, adenosine, guanosine and the corresponding 2'-deoxy ribo nucleosides (structure 6). (J. Heikkila, N. Balgobin and J. Chattopadhyaya, Acta Chem. Scand B 37, 857-864, 1983)

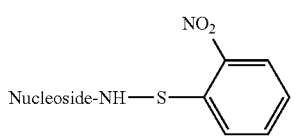

O-Nitrophenylsulfenyl Protecting Group

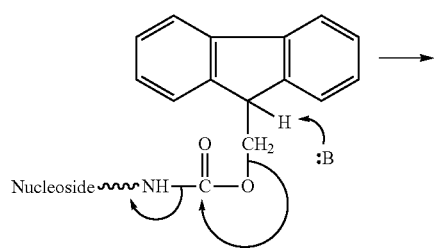

+ Liberated Nucleoside + $CO_2$

Scheme 1. Fmoc-B-Elimination Scheme

It is well known that cyanoethyl protecting group for internucleotide phosphate is eliminated by B-elimination mechanism leading to acrylonitrile and phosphodiester oligonucleotides. (scheme 2).

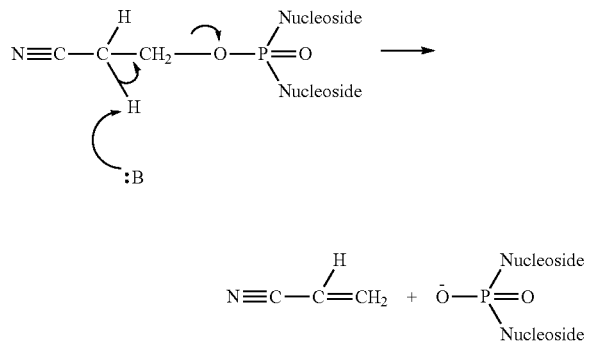

Scheme 2. Elimination of Cyanoethyl Phosphate Group

Schemes 1 & 2 suggest that it is possible to modulate the FMOC protecting group removal conditions from oligonucleotides. In fact, the FMOC as base protecting group can be removed by the process of B-elimination, just like the B-elimination process to remove cyanoethyl group.

This process therefore offers very attractive potential to use ammonia free oligo synthesis. Furthermore, this process has the potential to offer deoxyoligonucleotides for complete deprotection of oligos on solid supports, holdinging great promise for chip based technology. This process and technology have the potential to offer ribonucleotides such as required for chip based technology as well high purity oligonucleotides for microRNA, Si RNA, RNA chips.

The FMOC group, in conjunction with cyanoethyl phosphate protecting group, therefore allows the removal of both FMOC and cyanoethyl groups from the synthesized deoxy and ribo oligonucleotides on the support cleanly, with preferable non aq bases, and on support, all of which properties are useful for many diagnostics applications.

The utility of N-FMOC protected nucleoside has additional significance and importance: When oligo ribonucleotide chimeras comprise mixed bases composed of 2'-fluoro and 2'-ribo bases, they present a challenge in obtaining pure chimera oligonucleotides. It has been well documented by several recent reports that oligonucleotide chimeras having 2'-fluoro-2;'-deoxy bases along with natural ribo bases present a difficulty in obtaining pure oligos. It has been shown that with strongly basic conditions, there is significant loss of fluorine as loss of HF is seen as M–20 peak in Mass spectral analysis. It has also been shown that uracil and cytosine are eliminated to significant extent, when oligo chimeras containing 2'-fluoro-2'-deoxy uridine and 2'-fluoro-2'-deoxy cytidine are part of the chimeras (see scheme 3).

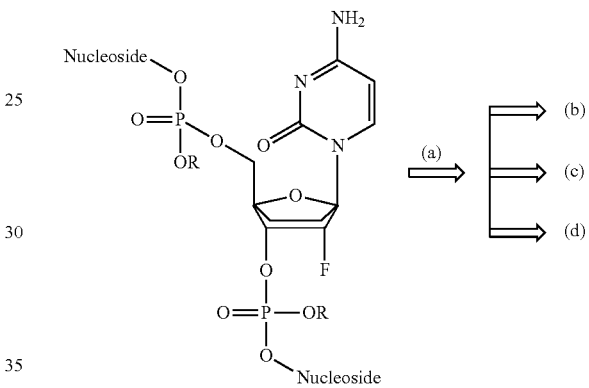

Scheme 3. Graphic Representation of effect on quality of oligonucleotides containing 2'-fluoro nucleosides: (a) deprotection using methyl amine, the usual deprotection condition of protecting groups of bases, (b) loss of fluorine leading to loss of HF, generating significant amount of M–20, (c) loss of cytosine and uracil, the pyrimidine bases is observed quite frequently, d) with the loss of pyrimidine, subsequent cleavage of chain occurs.

The studies as shown in scheme 3 were carried out independently by two groups recently:

Ken Hill, Agilent Technologies, Boulder, Colo.; Identification of Process Related Impurities—Understanding Oligonucleotide Production, TIDES 2007, Las Vegas. Nev. where the author showed depyrimidation of chimera oligonucleotides carrying 2'-fluoro-2'-deoxy pyrimidine in RNA's; and, Nanda D. Sinha, Avecia Biotechnologies Inc., Massachusetts-Depyrimidation, as well as loss of HF and chain cleavage in chimeras having 2'-fluoro-2'-deoxy pyrimidines in RNA sequences. Eurotides, 2005, Munich, Germany.

In order to overcome these difficulties, therefore, it is necessary to develop 2'-fluoro-2'-deoxy nucleosides and corresponding phosphoramidites with the base protecting groups incorporating N-FMOC protecting group, structures for mild deprotection group, preferably via B-elimination pathway so as to maintain integrity of oligo chimeras and attain requisite high quality for therapeutic and diagnostic applications.

(Structure 12)

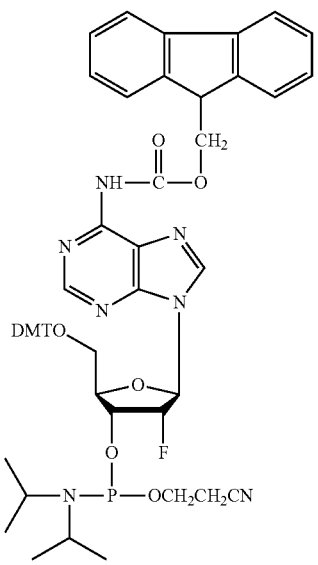

5'-DMT-N6-Fmoc-2'-fluoro-
2'dA-p-CED-phosphoramidite (Structure 13)

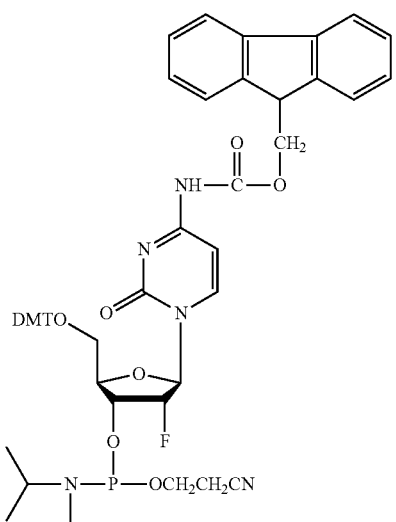

5'-DMT-N4-Fmoc-2'-fluoro
2'dC-p-CED-phosphoramidite (Structure 14)

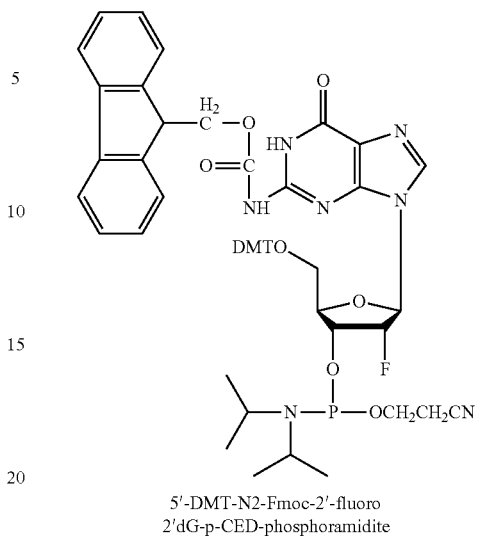

5'-DMT-N2-Fmoc-2'-fluoro
2'dG-p-CED-phosphoramidite

Besides the 2'-fluoro nucleosides, 2'-O-alkyl nucleoside phosphoramidites are extensively used in the design of biologically active oligonucleotides for therapeutic and diagnostic applications as fully alkylated or as chimeras. Amongst the 2'-O-alkyl nucleosides and phosphoramidites the most common are 2'-O-Methyl oligonucleotides which have shown enormous promise in drug design and specific diagnostics applications. Thus 2'-Omethyl oligoribonucleotides-RNA complexes have higher Tm than corresponding oligo-deoxy ribonucleosides-RNA duplexes, Iribarren, A. M., Sproat, B. S., Neuner, P., Sulston, I., Ryder, U., and Lamond, A. I., Proc. Natl. Acad. Sci. USA 87, 7747-7751, 1990. Various 2'-OMethyl-N-FMOC protected nucleosides and phosphoramidites offer great advantage in producing high quality of DNA-RNA oligonucleotides and chimera for biological applications.

Defined sequence RNA synthesis is now well established and currently in use for the synthesis and development of vast variety of therapeutic grade RNA aptamers, tRNA's, Si RNA and biologically active RNA molecules. This approach utilizes (as component 1) a ribonucleoside with suitable N-protecting group, generally a 5'-Protecting group, the most popular being dimethoxytriphenyl (DMT) group; a 2'-protecting group, the most popular being t-Butyldimethylsilyl ether; or a 3'-phosphoramidite, the most popular being cyanoethyl diisopropyl (component 1).

This component is then coupled with a nucleoside with a suitable N-protecting group, 2' or 3' succinate of a ribonucleoside attached to a solid support. The present invention represents an advance over prior art by achieving this coupling in solid support; the coupling of component 1 and 5'-OH-n-protected-2',3'-protected-nucleoside are also achieved in solution phase in the presence of an activator to lead to dimers and oligoribonucleotides, followed by oxidation (3→5' direction synthesis), also lead to protected dinucleoside having a 3'-5'-internucleotide linkage, Ogilvie, K. K., Can. J. Chem., 58, 2686, 1980.

It is by now recognized that the N-FMOC protecting group offers great potential in RNA synthesis of defined sequence.

This group can be utilized in conjunction with various 2'-protecting groups required for RNA synthesis. The most widely utilized 2'-protecting, tert-butyl-dimethylsilyl, which has been extensively developed by Ogilvie and coworkers as 2'-hydroxy protecting group for oligo ribonucleotide synthesis (Ogilvie, K. K., Sadana, K. L, Thompson, E. A., Quilliam, M. A., and Westmore, J. B *Tetrahedron Letters*, 15, 2861-2864, 1974; Ogilvie, K. K., Beaucage, S. L, Entwistle, D. W., Thompson, E. A., Quilliam, M. A., and Westmore, J. B. *J. Carbohydrate Nucleosides Nucleotides*, 3, 197-227, 1976;

Ogilvie, K. K. Proceedings of the 5th International Round Table on Nucleosides, Nucleotides and Their Biological Applications, Rideout, J. L., Henry, D. W., and Beacham L. M., III, eds., Academic, London, pp. 209-256, 1983).

These studies subsequently have led to continued developments of methods amenable to both solution and solid phase oligonucleotide synthesis, starting with the first chemical synthesis of RNA molecules of the size and character of tRNA (Usman, N., Ogilvie, K. K., Jiang, M.-Y., and Cedergren, R. J. *J. Am. Chem. Soc.* 109, 7845-7854, 1987; Ogilvie, K. K., Usman, N., Nicoghosian, K, and Cedergren, R. J. *Proc. Natl. Acad. Sci. USA,* 85, 5764-5768, 1988; Bratty, J., Wu, T., Nicoghosian, K., Ogilvie, K. K., Perrault, J.-P., Keith, G. and Cedergren, R., *FEBS Lett.* 269, 60-64, 1990). The literature has been comprehensively reviewed in: Gait, M. J., Pritchard, C. and Slim, G., Oligonucleotides and Their Analogs: A Practical Approach (Gait, M. J., ed.), Oxford University Press Oxford, England, pp 25-48, 1991.

Several other protecting groups have been lately employed for RNA synthesis. These include: bis(2-acetoxyethyl-oxy) methyl (ACE), Scaringe, S. A., Wincott, F. E., Caruthers, M. H., J. Am. Chem. Soc., 120: 11820-11821, 1998; triisopropylsilyloxy methyl (TOM), Pitsch, S., Weiss, P. A., Jenny, L., Stutz, A., Wu, X., Hely. Chim. Acta. 84, 3773-3795, 2001; and t-butyldithiomethyl (DTM) (structure 16), Semenyuk, A., Foldesi, A., Johansson, T., Estmer-Nilsson, C., Blomgren, P., Brannvall, M., Kirsebom, L. A., Kwiatkowski, M., J. Am. Chem. Soc., 128: 12356-12357, 2006.

A more recent invention by the scientists at ChemGenes Corporation developed a patent-pending method for the synthesis of RNA in the reverse direction (i.e., 5'→3'direction) for incorporation of many ligands and chromophores conveniently and efficiently at the 3'-end of the RNA molecules. With this approach, appropriate N-FMOC protected nucleosides, deoxy and ribo may be synthesized utilizing the many advantages of "reverse direction synthesis" of DNA and RNA some of which are briefly mentioned at the end of this section.

A novel 2'-protecting group, acetal levulinyl ester (ALE) (structure 15) has been recently proposed (J. G. Lackey and M. J. Damha, Nucleic Acids Symposium Series, No. 52, 35-36, 2008). Similar to this protecting group another 2'-labile protecting group based on similar chemical nature, 2'-O-acetal ester, pivaloyloxy methyl which has been found mild 2'-O protecting group, T. Layergne, A. Martin, F. Debart, J- J Vasseur, Nucleic Acids Symposium Series No. 52, 51-52, 2008. The base protecting group used by these authors was however n-acetyl and tBpac. However N-Fmoc would be an ideal group for deprotection under mild basic or non basic conditions such as a tertiary amine.

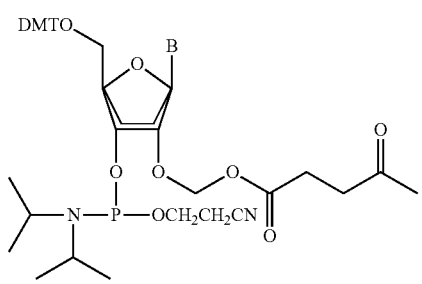

2'-O-ALE-N-Fmoc amidites (structure 15)

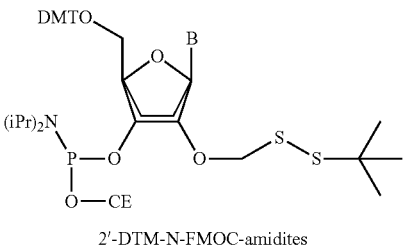

2'-DTM-N-FMOC-amidites (structure 16)

Chemically modified RNA has been synthesized having modified arabino sugars, 2'-deoxy-2'-fluoro-beta-D_arabinonucleic acid (FANA; structure 17) and 2'-deoxy-4'-thio-2'-fluoro-beta-D_arabinonucleic acid (4'-Thio-FANA; structure 18) into sequences for SiRNA activities (Dowler, T., Bergeron, D., Tedeschi, Anna-Lisa, Paquet, L., Ferrari, N., Damha, M. J., Nucl. Acids Res., 34, 1669-1675, 2006). Amongst several new 2'-protecting groups which have been developed, the 2'-protecting 2-cyanoethoxymethyl (CEM) (structure 19) has been shown to produce very long RNA by carrying out RNA synthesis in the conventional (3'→5') direction. However, the quality of these long RNA's remains in question.

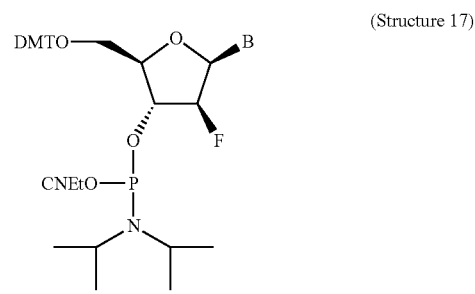

2'-F-ANA modified phosphoramidites (Structure 17)

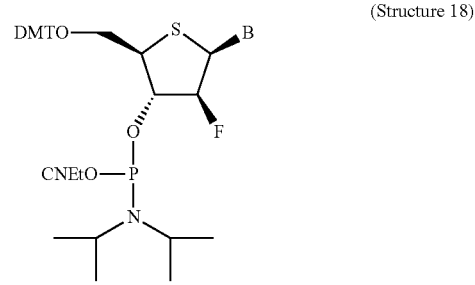

4'-Thio-2'-F-ANA modified phosphoramidites (Structure 18)

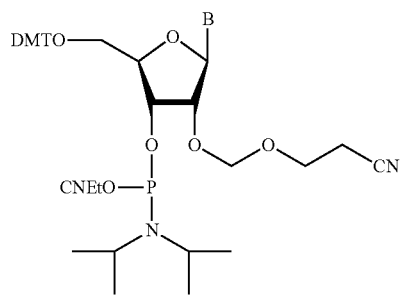

2'-CEM Protected RNA Intermediates (Structure 19)

But the N-FMOC protected nucleosides having the 2'-protecting group discussed above can be combined and utilized for high purity RNA synthesis. The N-FMOC protecting group offers great potential in RNA synthesis of defined sequence. This includes RNA synthesis in the conventional direction (3'→5' direction as well as using newly discovered 5'→3' direction, i.e., reverse direction synthons; structures 20, 21 & 22).

Structures of Reverse Phosphoramidites and Solid Supports:

(Structure 20)

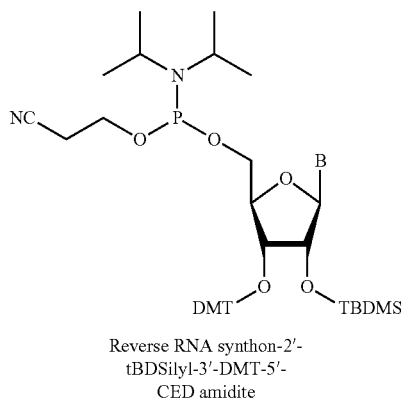

Reverse RNA synthon-2'-
tBDSilyl-3'-DMT-5'-
CED amidite (Structure 21)

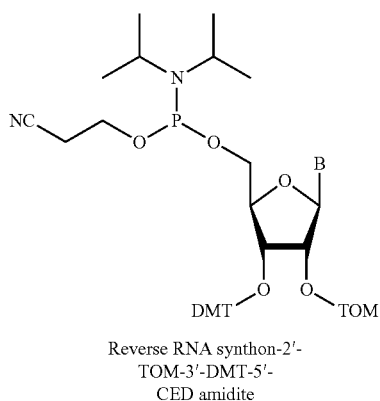

Reverse RNA synthon-2'-
TOM-3'-DMT-5'-
CED amidite (Structure 22)

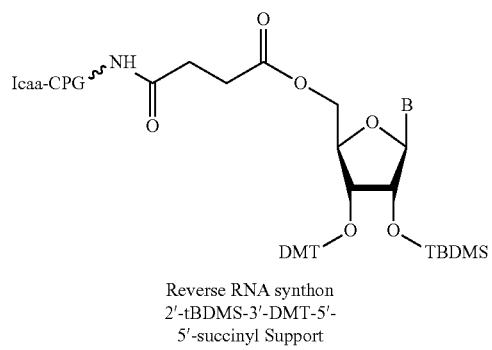

Reverse RNA synthon
2'-tBDMS-3'-DMT-5'-
5'-succinyl Support

Where B = A (N—Bz), C (N—Bz), C (N—Ac), G (N—Ac), U.

Chemical synthesis of RNA is desirable because it avoids the inefficiencies and limitation of scale of synthesis such as those introduced by in vitro transcription by T7 RNA polymerase (Helm, M., Brule, H., Giege, R., Florence, C., RNA, 5:618-621, 1999). Chemical synthesis of RNA is particularly desirable for studies of RNA structure and function, and many useful modifications can be achieved selectively, such as site specific introduction of functional groups, viz., disulphide cross linking as a probe of RNA tertiary structures (Maglott, E. J., Glick, G. D., Nucl. Acids Res., 26: 1301-1308, 1999).

Synthesis of long RNA is very important for biologically active molecules such as tRNA, and such synthesis have been achieved (Persson, T., Kutzke, U., Busch, S., Held, R., Harmann, R. K., Bioorgan. Med. Chem., 9:51-56, 2001; Oglvie, K. K., Usman, N., Nicoghosian, K., Cedrgren, R. J., Proc. Natl. Acad. Sci., USA, 85:5764-5768, 1988; Bratty, J., Wu, T., Nicoghosian, K., Ogilvie, K. K., Perreault, J.- P., Keith, G., Cedergren, R. J., F.E.B.S. Lett., 269:60-64, 1990; Gasparutto, D., Livache, T., Bazin, H., Duplaa, A. M., Guy, A., Khorlin, A., Molko, D., Roget, A., Teoule, R., Nucl. Acids. Res., 20:5159-5166, 1992; Goodwin, J. T., Stanick, W. A., Glick, G. D., J. Org. Chem., 59:7941-7943, 1994).

The aforementioned techniques of RNA synthesis in reverse direction (5'→3' direction) make the introduction of a number of groups required for selective introduction at 3'-end practical and convenient. The experimental data at Chem-Genes Corp. showed higher coupling efficiency per step during automated oligo synthesis with reverse RNA amidites (structures 21, 22, 23), and therefore greater ability to achieve higher purity and to produce very long oligos. It was also demonstrated that the process of the present invention leads to oligonucleotides free of M+1 species, which commonly lead to closer impurities as shoulder near desired peak during HPLC analysis or purification or Gel purification. Such reverse RNA structures replacing the standard n-protecting group with n-FMOC protecting group offer additional unforeseen advantages.

SUMMARY OF THE INVENTION

The present invention discloses novel -N-FMOC protected nucleosides, succinates, phosphoramidites, corresponding solid supports that are suitable for oligo deoxy nucleosides and RNA oligonucleotide synthesis.

The novel use of N-FMOC as nucleoside base protecting group, which is highly base labile protecting group, is a novel approach that leads to very high purity and very clean oligonucleotide after the removal of the protecting groups, and provides efficient process for producing high purity, therapeutic grade DNA oligonucleotides, RNA oligonucleotides, diagnostic DNA, diagnostic RNA for platform.

The deprotection of FMOC protecting groups of the natural deoxy and ribonucleosides occurs under the mildest possible deprotection conditions, and the removal of such groups under very mild conditions allows synthesis of various DNA and RNA of highest purity for diagnostics and therapeutic application. This approach is further designed to use FMOC protecting group on various base sensitive nucleoside, and for use in oligo peptide synthesis.

Defined sequence RNA synthesis is now well established and currently in use for synthesis and development of vast variety of therapeutic grade RNA aptamers, tRNA's, Si RNA and biologically active RNA molecules. This approach utilizes a ribonucleoside with suitable N-protecting group, 5'-Protecting group, generally and most popular being dimethoxytriphenyl, commonly called DMT group, 2'-protecting group, out of which most popular being t-Butyldimethylsilyl ether and a 3'-phosphoramidite, the most popular being cyanoethyl diisopropyl (component 1). This component is then coupled with a nucleoside with a suitable N-protecting group, 2' or 3' succinate of a ribonucleoside attached to a solid support (component 2). The coupling of component 1 and 5'-OH-n-protected-2',3'-protected-nucleoside (component 3) are also achieved in solution phase in the presence of an activator to lead to dimers and oligoribonucleotides, followed by oxidation (3'→5' direction synthesis), also lead to protected dinucleoside having a 3'-5'-internucleotide linkage, Ogilvie, K. K., Can. J. Chem., 58, 2686, 1980 (scheme 1).

For the N-FMOC nucleoside protecting group the widely utilized 2'-protecting which has been extensively developed by Ogilvie and coworkers as 2'-hydroxy protecting group for oligo ribonucleotide synthesis (Ogilvie, K. K., Sadana, K. L, Thompson, E. A., Quilliam, M. A., and Westmore, J. B *Tetrahedron Letters,* 15, 2861-2864, 1974; Ogilvie, K. K., Beaucage, S. L, Entwistle, D. W., Thompson, E. A., Quilliam, M. A., and Westmore, J. B. *J. Carbohydrate Nucleosides Nucleotides,* 3, 197-227, 1976; Ogilvie, K. K. Proceedings of the 5th International Round Table on Nucleosides, Nucleotides and Their Biological Applications, Rideout, J. L., Henry, D. W., and Beacham L. M., III, eds., Academic, London, pp. 209-256, 1983).

These studies subsequently led to continued developments of methods which were amenable to both solution and solid phase oligonucleotide synthesis, and the first chemical synthesis of RNA molecules of the size and character of tRNA (Usman, N., Ogilvie, K. K., Jiang, M.-Y., and Cedergren, R. J. *J. Am. Chem. Soc.* 109, 7845-7854, 1987; Ogilvie, K. K., Usman, N., Nicoghosian, K, and Cedergren, R. J. *Proc. Natl. Acad. Sci. USA,* 85, 5764-5768, 1988; Bratty, J., Wu, T., Nicoghosian, K., Ogilvie, K. K., Perrault, J.- P., Keith, G. and Cedergren, R., FEBS Lett. 269, 60-64, 1990). The literature has been amply reviewed in subsequent excellent publication: Gait, M. J., Pritchard, C. and Slim, G., Oligonucleotides and Their Analogs: A Practical Approach (Gait, M. J., ed.), Oxford University Press Oxford, England, pp 25-48, 1991. Other protecting groups which have been lately employed for RNA synthesis are; bis(2-acetoxyethyl-oxy)methyl (ACE), Scaringe, S. A., Wincott, F. E., Caruthers, M. H., J. Am. Chem. Soc., 120: 11820-11821, 1998; triisopropylsilyloxy methyl (TOM), Pitsch, S., Weiss, P. A., Jenny, L., Stutz, A., Wu, X., Hely. Chim. Acta. 84, 3773-3795, 2001 and t-butyldithiomethyl (DTM) (structure 1), Semenyuk, A., Foldesi, A., Johansson, T., Estmer-Nilsson, C., Blomgren, P., Brannvall, M., Kirsebom, L. A., Kwiatkowski, M., J. Am. Chem. Soc., 128: 12356-12357, 2006 have been introduced. However none of these are amenable to carry out the synthesis in reverse direction (5'→3'direction), and hence lack the capability of introduction of many ligands and chromophores conveniently and efficiently at the 3'-end of RNA molecules.

The present invention is directed towards the synthesis of high purity RNA's and specifically to introduce nucleosidic or non-nucleosidic bases, which are labile in nature for synthesis of synthetic RNA's. Such RNA's have vast application in therapeutics, diagnostics, drug design and selective inhibition of an RNA sequence within cellular environment, blocking a function of different types of RNA present inside cell. Silencing gene expression at mRNA level with nucleic acid based molecules is fascinating approach. Among these RNA interference (RNAi) has become a proven approach which offers great potential for selective gene inhibition and showing great promise for application in control and management of various biochemical and pharmacological processes. Early studies by Fire et al., Fire, A., Xu, S., Montgomery, M. K., Kostas, S. A., Driver, S. E., and Mello, C. C, Nature, 391, 806-811, 1998, showed that RNA interference in *Caenorhabditis elegans* is mediated by 21 and 22 nucleotide RNA sequences. This was further confirmed as general phenomenon of specific inhibition of gene expression by small double stranded RNA's being mediated by 21 and 22 nucleotide RNA's, Genes Dev., 15, 188-200, 2001. Simultaneous studies by Capie, N. J., Parrish, S., Imani, F., Fire, A., and Morgan, R. A., confirmed such phenomenon of specific gene expression by small double stranded (dS) RNAs in invertebrates and vertebrates alike. Subsequently a vast amount of research led to confirmation of above studies and established RNAi as a powerful tool for selectively and very specific gene inhibition and regulation, Nishikura, K., Cell, 107, 415-418, 2001; Nykanen, A., Haley, B., Zamore, P. D., Cell, 107, 309-321, 2001; Tuschl, T., Nat. Biotechnol., 20, 446-448, 2002; Mittal, V., Nature Rev., 5, 355-365, 2004; Proc. Natl. Acad. Sci. USA, 99, 6047-6052, 2002; Donze, O. & Picard, D., Nucl. Acids. Res., 30, e46, 2002; Sui, G., Soohoo, C., Affar el, B., Gay, F., Shi, Y., Forrester, W. c., and Shi, Y., Proc. Natl. Acad. Sci. USA, 99, 5515-5520, 2002; Paddison, P. J., Caudy, A. A., Bernstein, E., Hannon, G. J., and Conklin, D. S., Genes Dev., 16, 948-959, 2002.

The FMOC group, in conjunction with cyanoethyl phosphate protecting group, therefore offers opportunity to remove both FMOC and cyanoethyl groups from the synthesized deoxy and ribo oligonucleotides on the support cleanly, with non aq bases, and on support, which properties are useful for many diagnostics application. Our present invention is revealed by structures such as 7-10 below.

Synthons for DNA Synthesis:

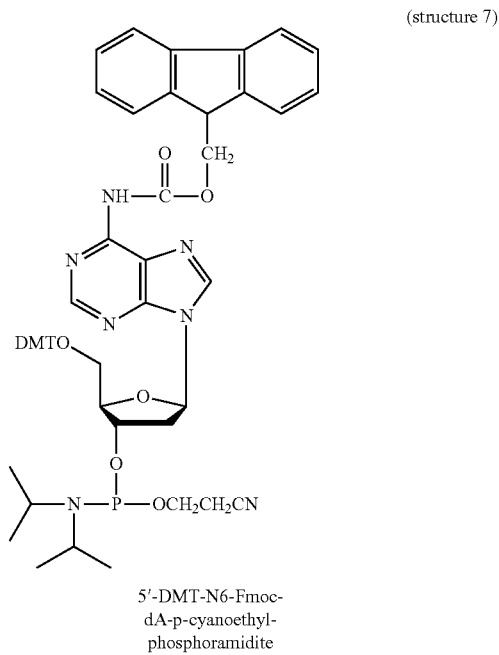

5'-DMT-N6-Fmoc-dA-p-cyanoethyl-phosphoramidite (structure 7)

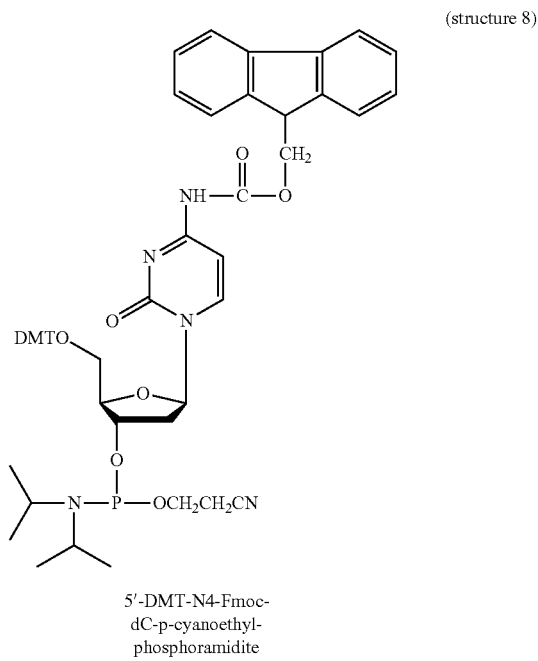

5'-DMT-N4-Fmoc-dC-p-cyanoethyl-phosphoramidite (structure 8)

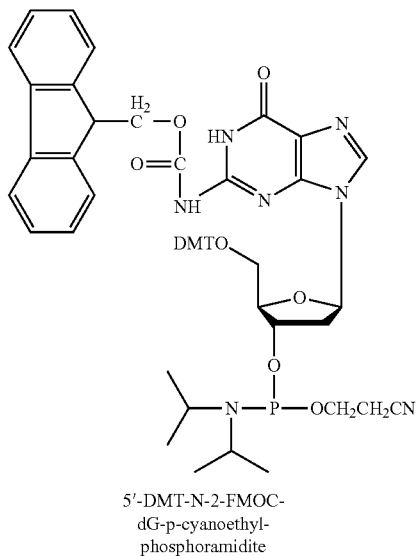

5'-DMT-N-2-FMOC-
dG-p-cyanoethyl-
phosphoramidite

Synthons for RNA Synthesis:

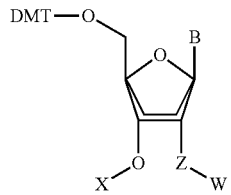

(General structure 10)

2'-tBD-N-Fmoc-
r-nucleoside-
phosphoramidites

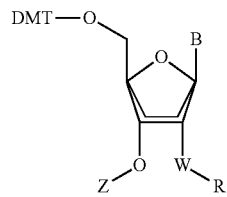

(General structure 11)

2'-TOM-N-FMOC
r-nucleoside
phosphoramidites

The present invention provides novel N-Fmoc protected nucleosides outlined in Formula 1 below. The synthetic route that has been developed allows obtaining desired nucleosides without any contamination with unwanted isomers. The N-FMOC protected nucleosides having the 2'-protecting group discussed above can be combined with cyanoethyl phosphate protecting group and utilized in high purity RNA synthesis (structure 9)

Formula 1
Where B=a) Adenine(N-Fmoc), b) Cytosine(N-Fmoc), c) Guanine(N-Fmoc), d) 5-methyl cytosine(N-Fmoc), e) 5-bromocytidine(N-Fmoc), i) 5-iodo cytosine(N-Fmoc), j) 5-fluorocytosine(N-Fmoc), k) 2,6-diaminopurine(N-Fmoc), l) 2-amino purine(N-Fmoc), Z=Oxygen & W is H; Z=Oxygen and W=tButyldimethyl silyl, TOM (triisopropyloxymethylene), acetal levulinyl ester (ALE), cyanoethylmethylene (CEM); DTM; X=a) cyanoethyl-dialkylphosphoramidite.

The nucleic bases in our invention protected with 9-fluorenylmethyloxycarbonyl protecting group (Fmoc). The solid support having protected nucleosides containing 5'-DMT group and 3' terminus is attached to solid support (Formula 2).

Formula 2:
Where B=a) Adenine(N-Fmoc), b) Cytosine(N-Fmoc), c) Guanine(N-Fmoc), d) 5-methyl cytosine(N-Fmoc), e) 5-bromocytidine(N-Fmoc), i) 5-iodo cytosine(N-Fmoc), j) 5-fluorocytosine(N-Fmoc), k) 2,6-diaminopurine(N-Fmoc), l) 2-amino purine(N-Fmoc), W=Oxygen and R=tButyldimethyl silyl, TOM (triisopropyloxymethylene), acetal levulinyl ester (ALE), cyanoethylmethylene (CEM); DTM; Z=a) succinimido long chain attached to a solid support, b) hydroquinone succinimido long chain spacer attached to solid support or c) oxalyl amido long chain spacer attached to solid support.

The nucleosides can be used in oligonucleotide synthesis. The base deprotection step can be performed in mild basic conditions or a tertiary amine capable of removal of Fmoc protecting group via B-elimination in solution phase or on solid support without oligonucleotide detachment.

The invention also contemplates delivery of kits that contain one or more of the disclosed nucleoside compositions.

Solvent System Eluent A—70% ACN in 0.1M TEAA [pH 7.5]; Eluent B—80%

ACN in 0.1M TEAA; Gradient: Increase B (0-50%) in 20 min;

Dissolved in: CAN, Flow Rate: 1.5 ml/min

Figures 1A, 1B:
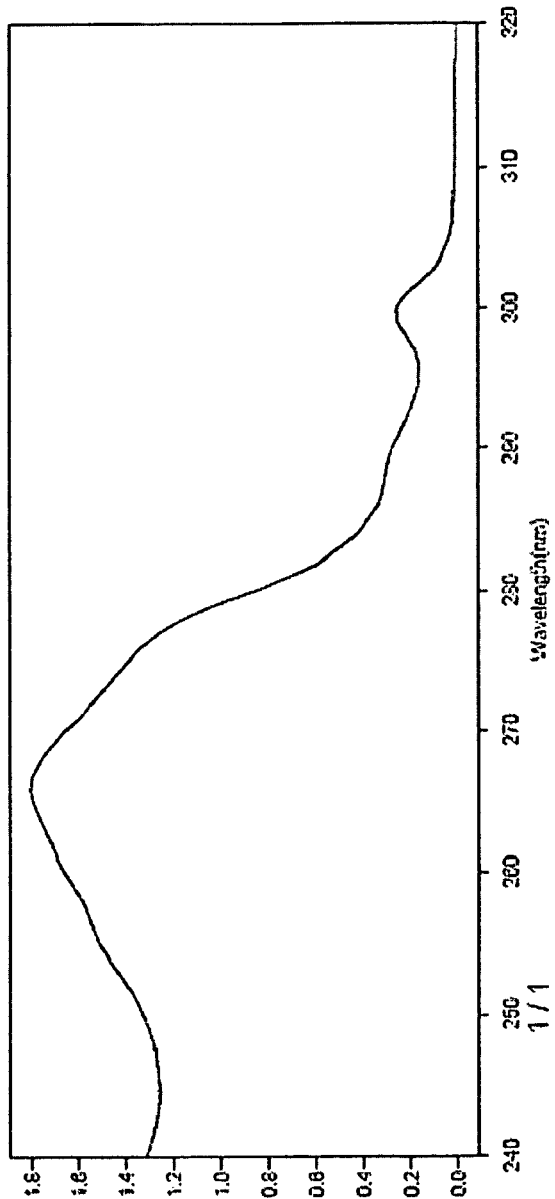
FIG. 1a. UV spectral analysis of 5'-DMT-N6-Fmoc deoxy Adenosine; solvent MeOH.
2.
FIG. 1b. UV spectral analysis report of 5'-DMT-N6-Fmoc deoxy Adenosine
3.
Figure 2:
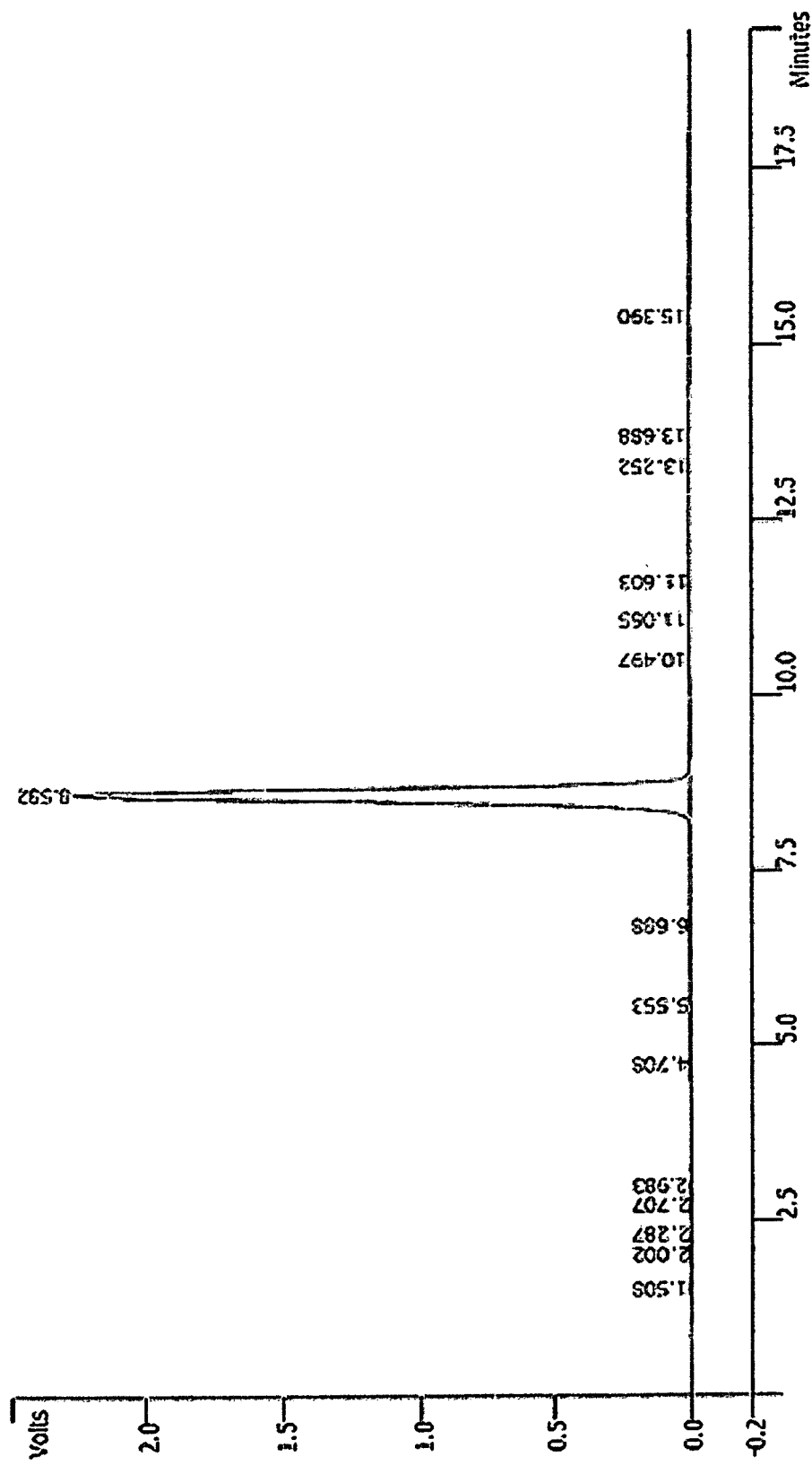
FIG. 2. HPLC analysis of 5'-DMT-N6-Fmoc deoxy Adenosine. HPLC CHROMATOGRAM—Purity 98.93%
HPLC Method Notes: Column: ChromSep SS (4.6×250 mm) with ChromSep;
Guard Column OmniSpher 5 C18; Detection: UV @254 nm.
Figure 3:
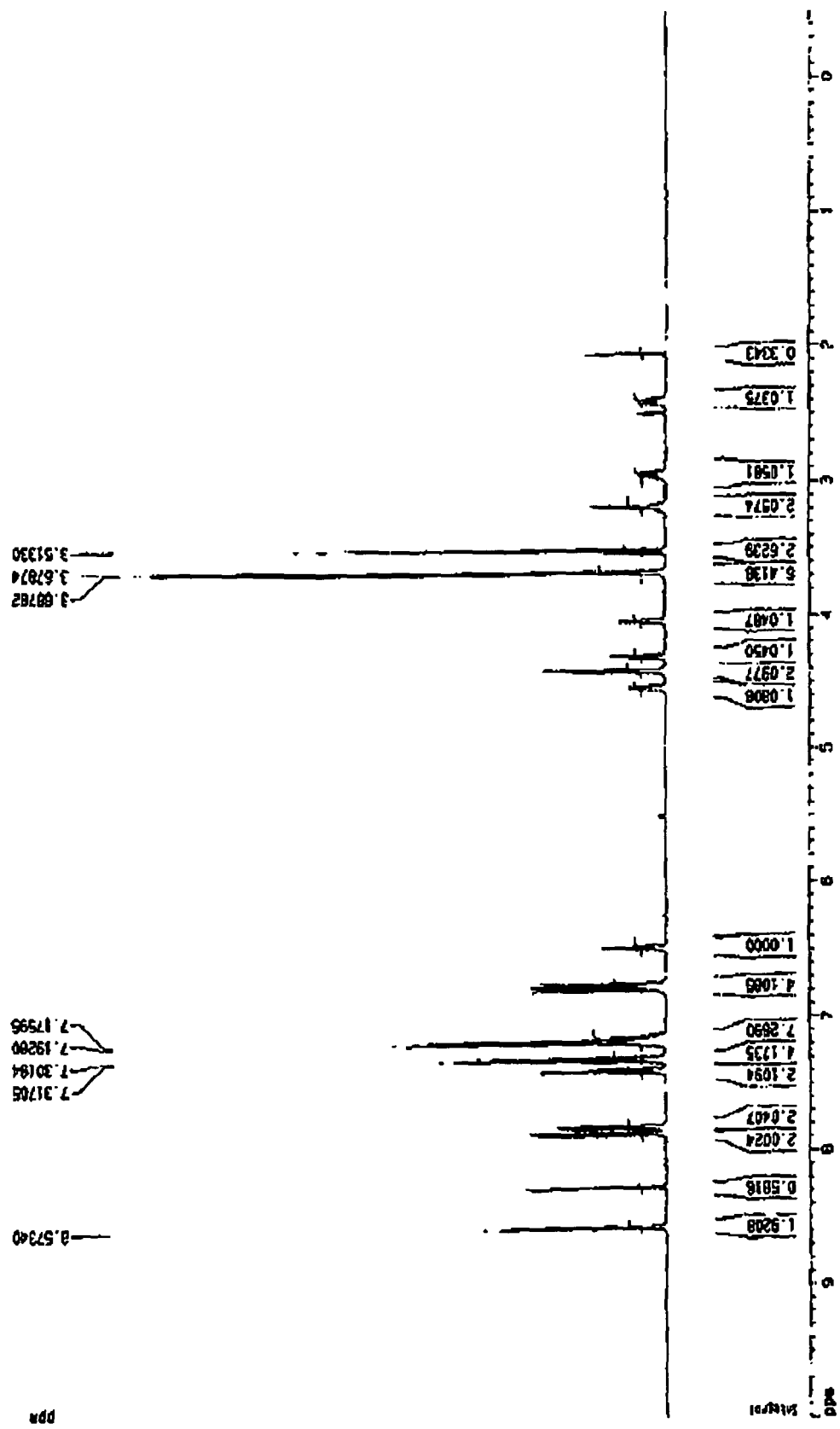
Figure 4:
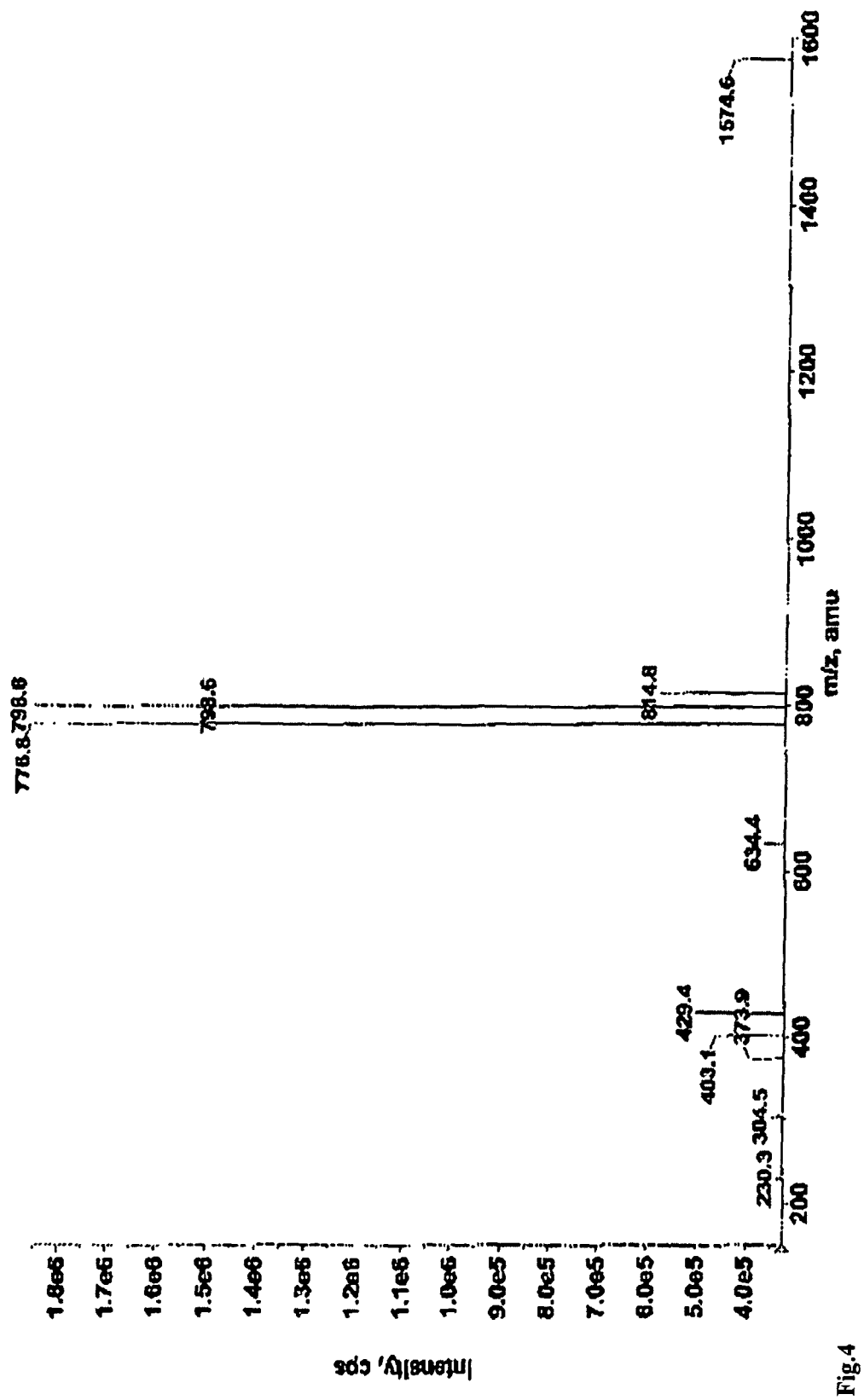
Figures 5A, 5B:
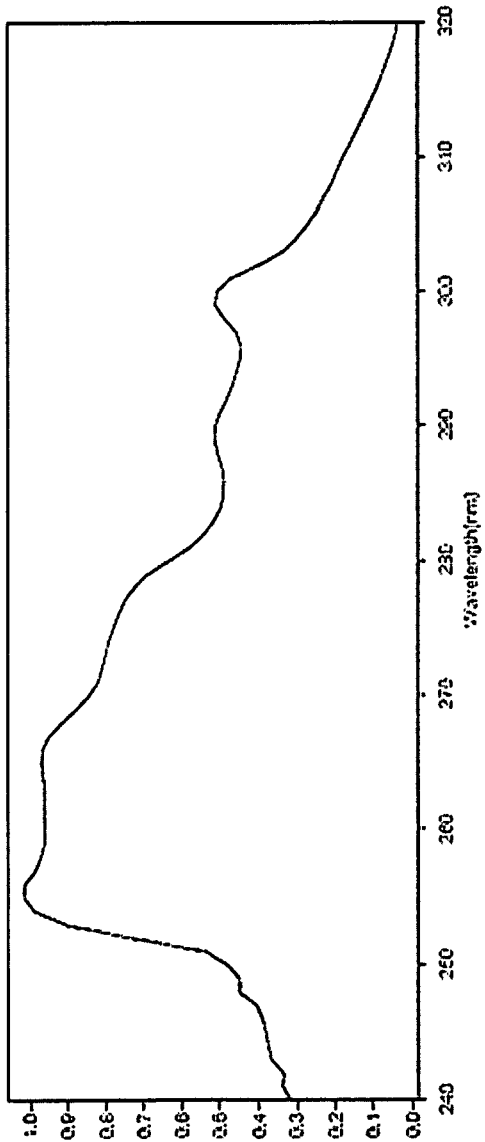

4. FIG. 3. 1H NMR analysis of 5'-DMT-N6-Fmoc deoxy Adenosine. 500 MHz—DMSO/D2O 5. FIG. 4. Mass spectral analysis (positive ion analysis) of 5'-DMT-N6-Fmoc deoxy Adenosine 6. FIG. 5*a*. UV spectral analysis of 5'-DMT-N4-Fmoc deoxy cytidine; solvent MeOH.

7. FIG. 5*b*. UV spectral analysis report of 5'-DMT-N4-Fmoc deoxy cytidine

Figure 6:
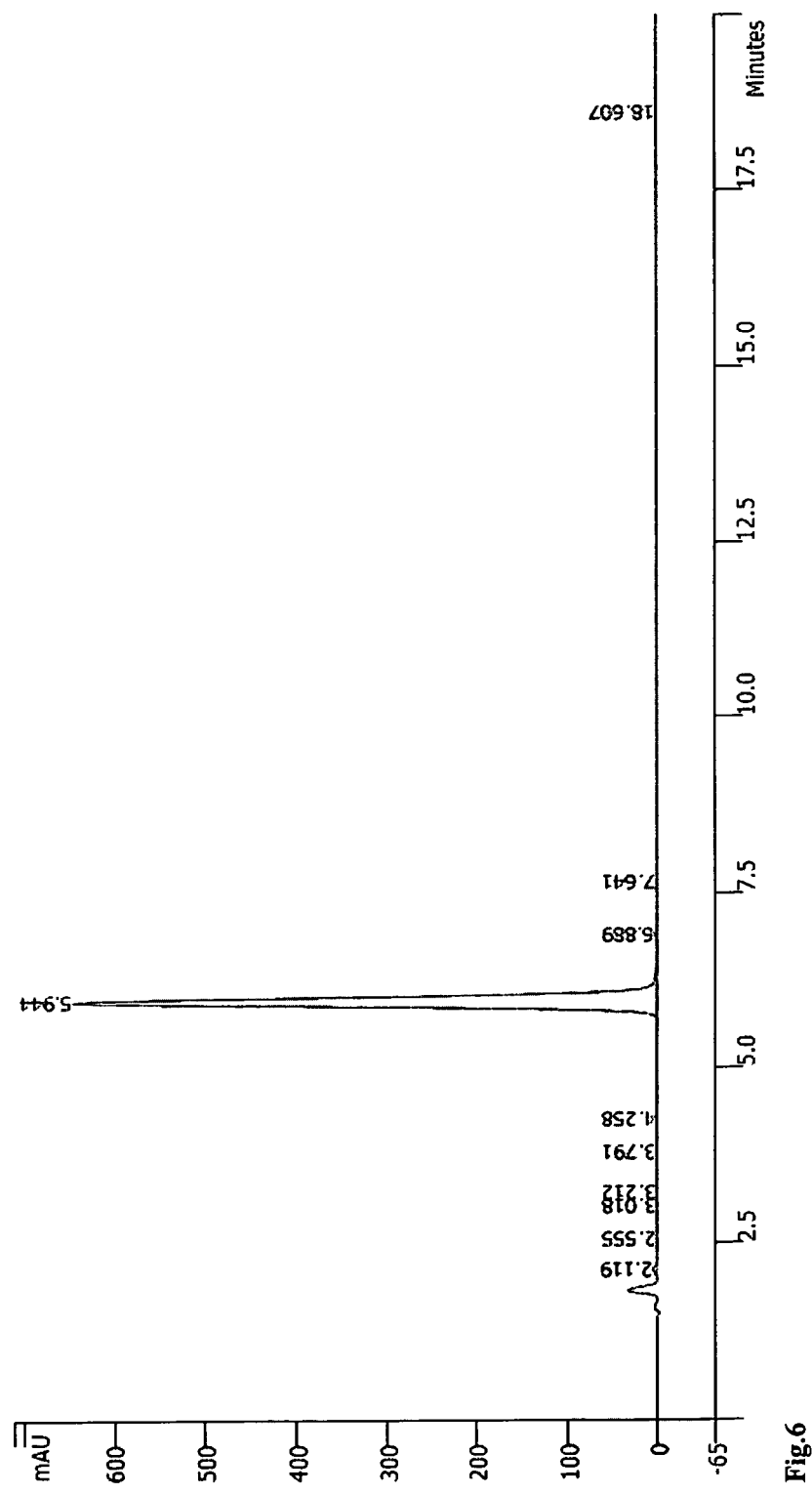

8. FIG. 6. HPLC analysis of 5'-DMT-N4-Fmoc deoxy cytidine HPLC CHROMATOGRAM—Purity 99.11%

HPLC Method Notes: Column: ChromSep SS (4.6×250 mm) with ChromSep;

Guard Column OmniSpher 5 C18; Detection: UV @254 nm

Solvent System Eluent A—80% ACN in 0.1M TEAA [pH 7.5]; Eluent B—90% ACN in 0.1M TEAA; Gradient: Increase B (0-50%) in 20 min;

Dissolved in: DMF:MeOH; Flow Rate: 1.5 ml/min

Figure 7:
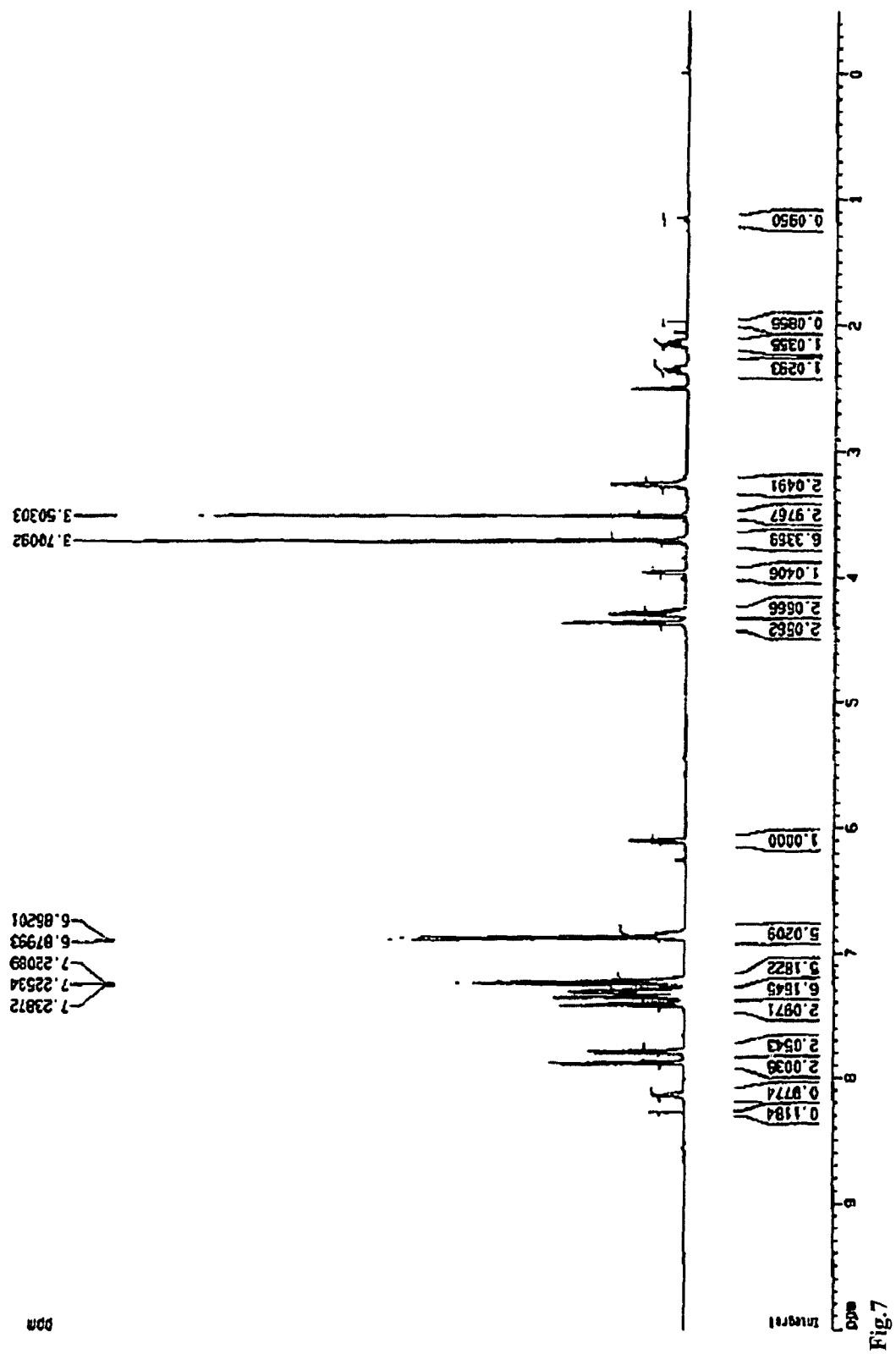
Figure 8:
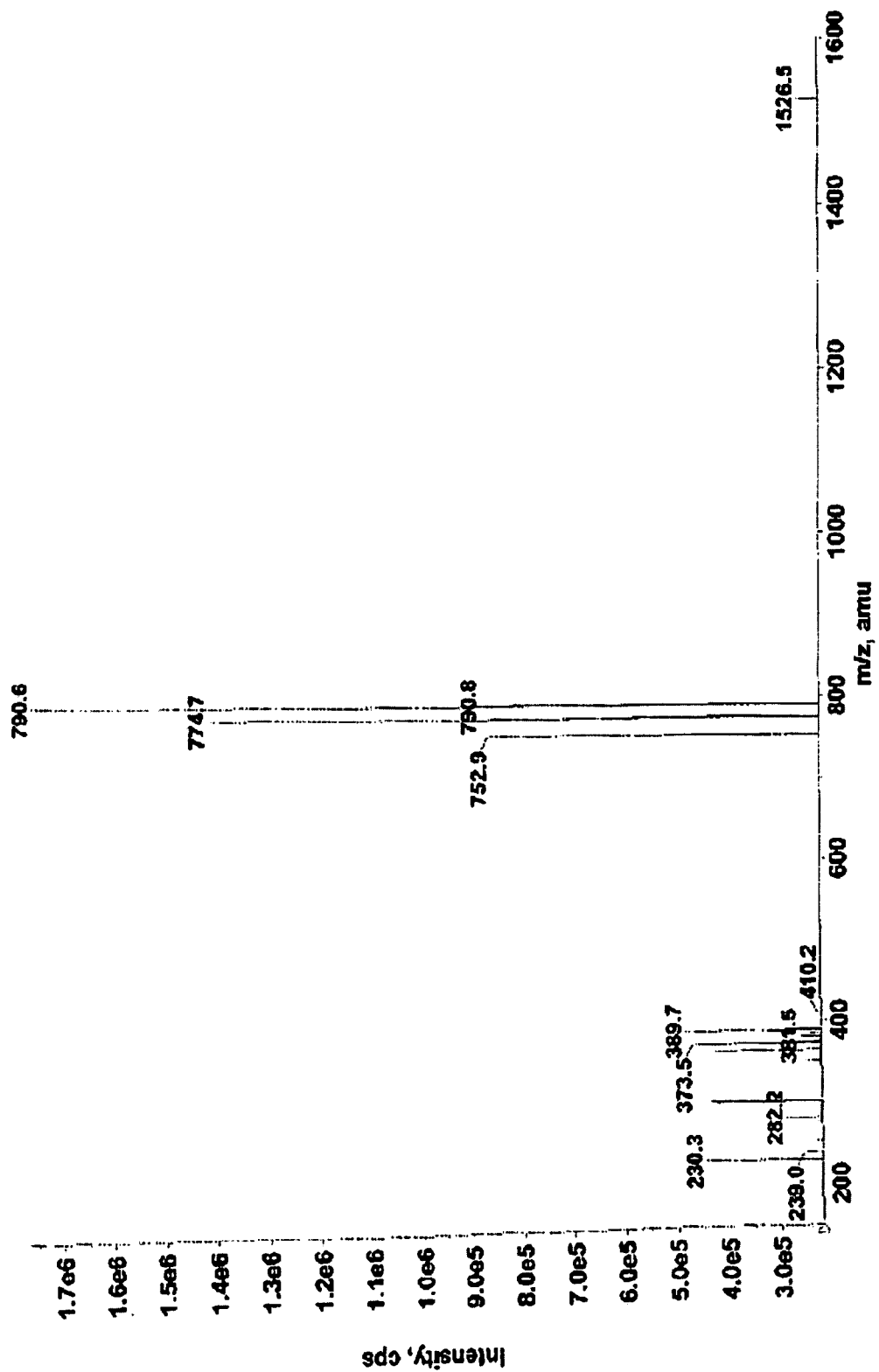

9. FIG. 7. 1H NMR analysis of 5'-DMT-N4-Fmoc deoxy cytidine. 500 MHz—DMSO/D2O 10. FIG. 8. Mass spectral analysis (positive ion analysis) of 5'-DMT-N4-Fmoc deoxy cytidine.

11. FIG. 9*a*. UV spectral analysis of 5'-DMT-N2-Fmoc deoxy guanosine; solvent MeOH.

Figure 9B:
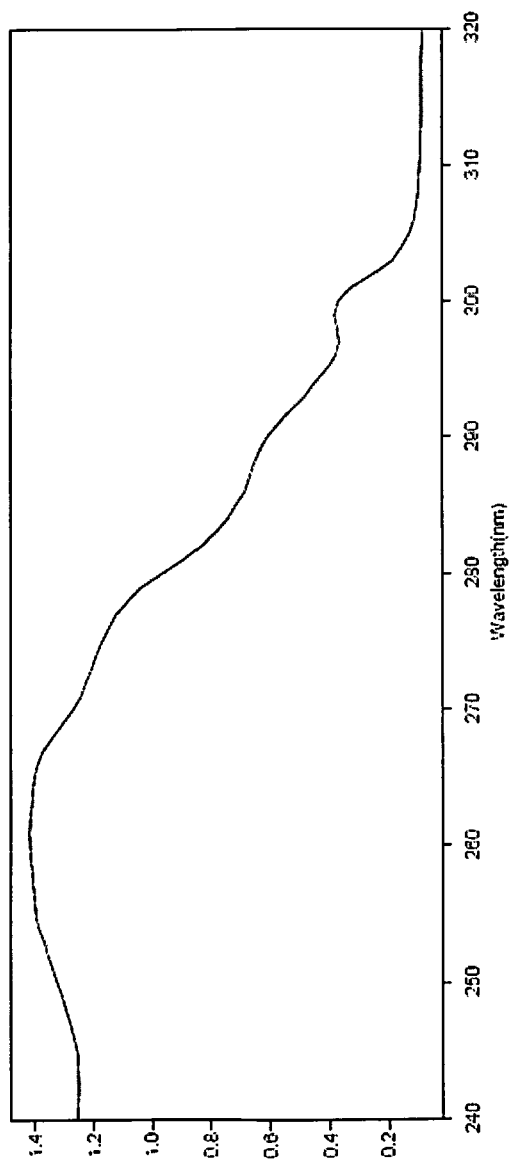

12. FIG. 9*b*. UV spectral analysis of 5'-DMT-N2-Fmoc deoxy guanosine

Figure 10:
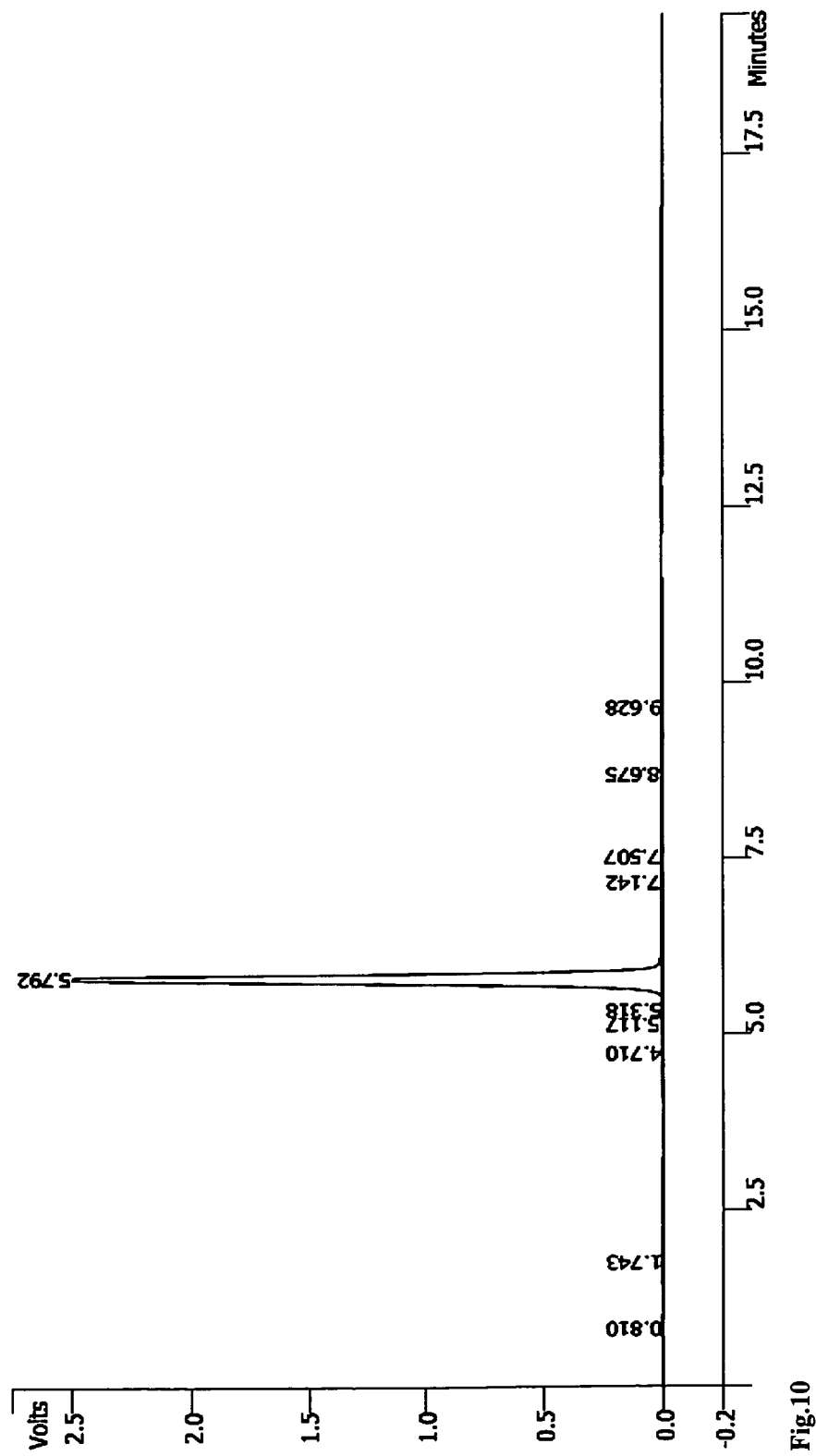

13. FIG. 10. HPLC analysis of 5'-DMT-N2-Fmoc deoxy guanosine HPLC CHROMATOGRAM Purity 99.02%

HPLC Method Notes: Column: ChromSep SS (4.6×250 mm) with ChromSep;

Guard Column OmniSpher 5 C18; Detection: UV @ 254 nm

Figure 11:
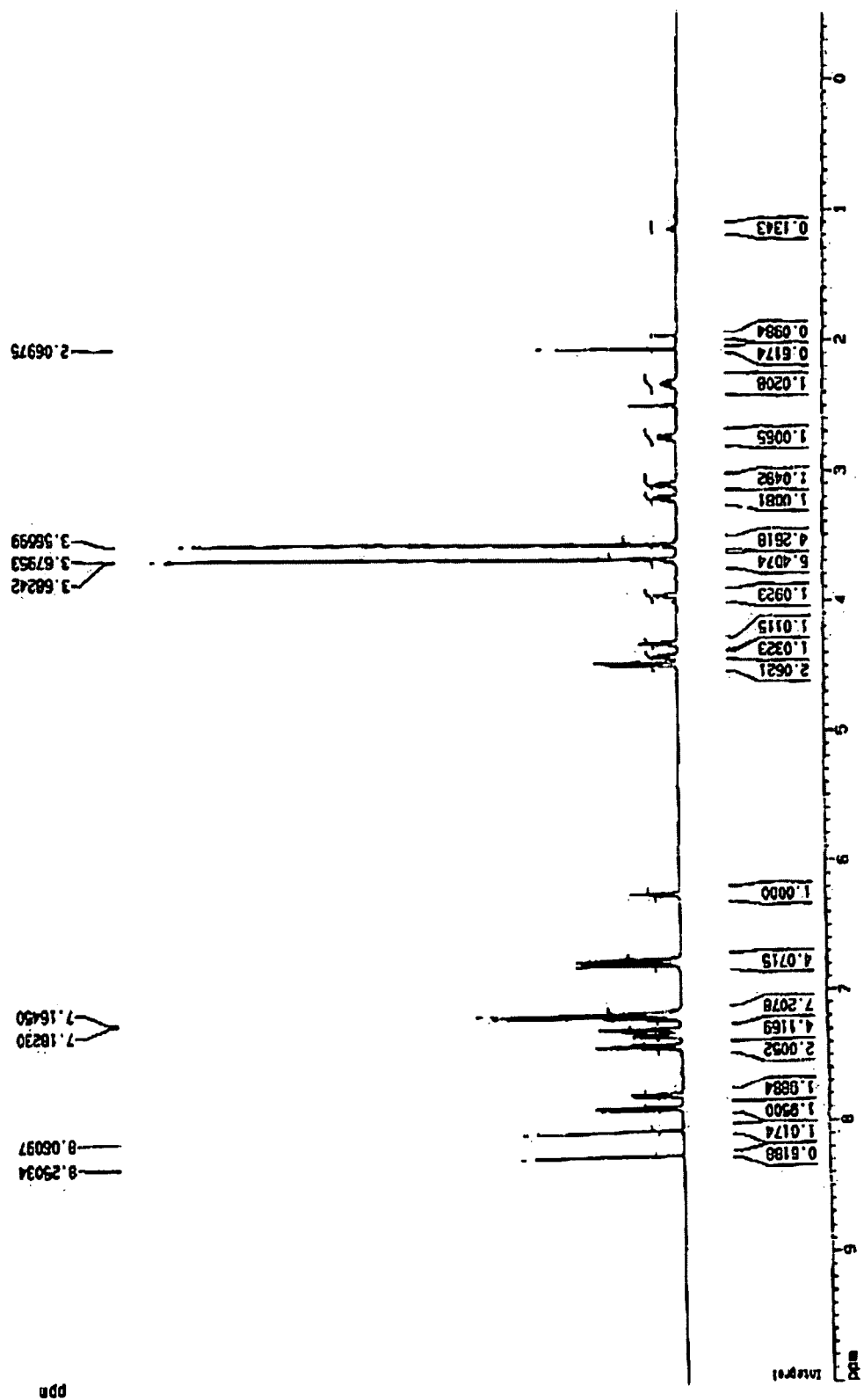
Figure 12:
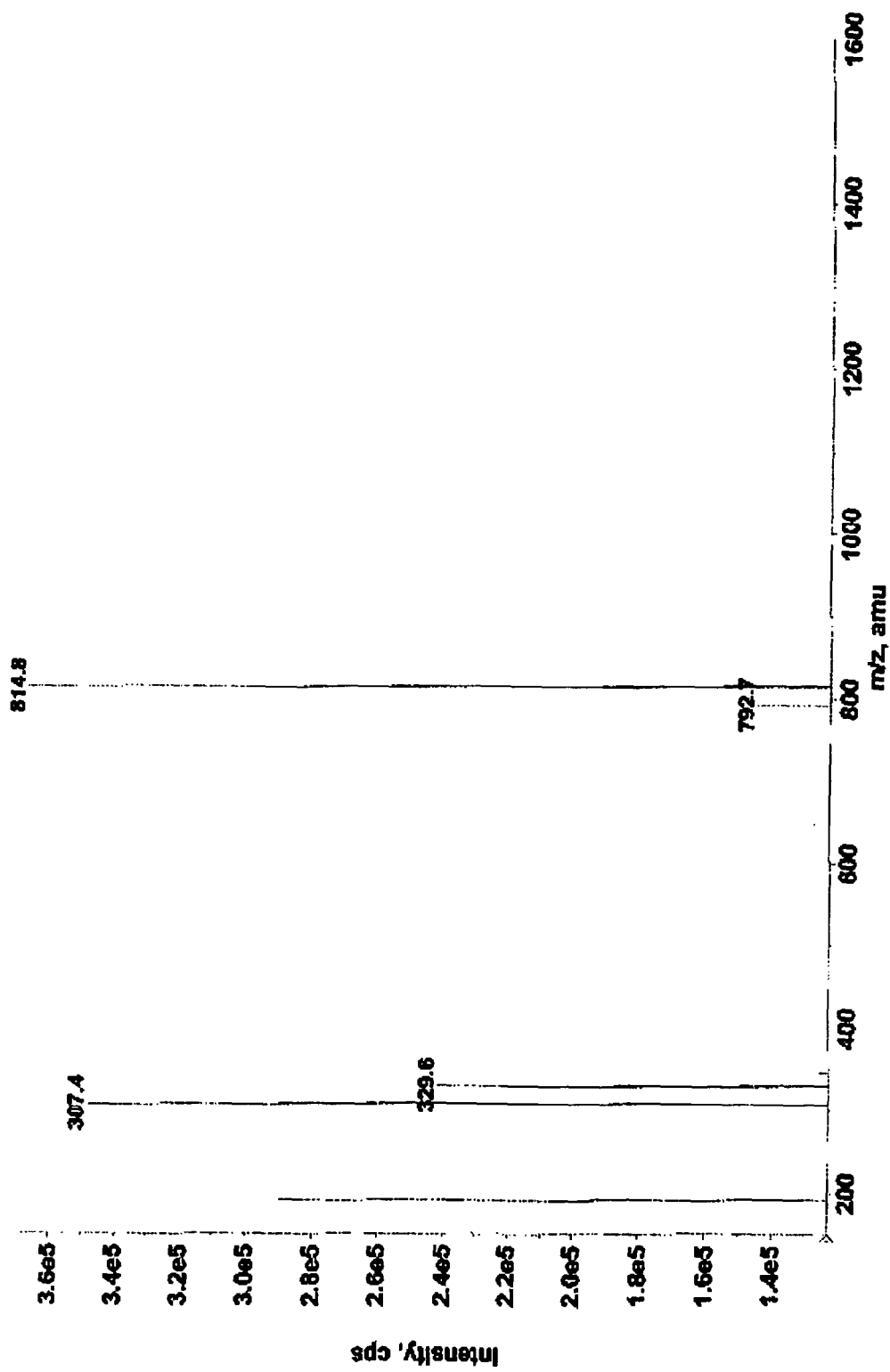
Figure 13:
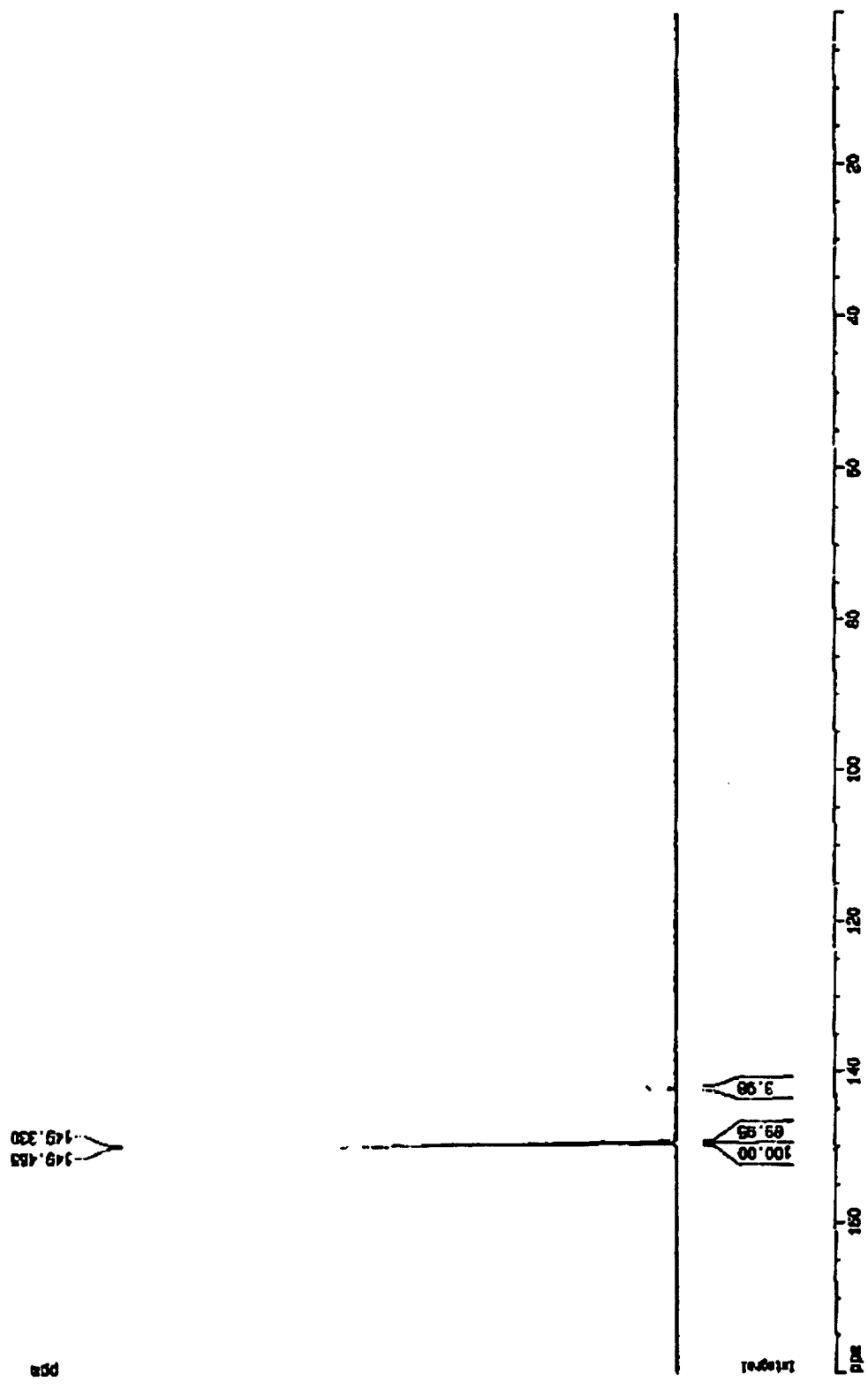

Solvent System: Eluent A—70% ACN in 0.1M TEAA [pH 7.5]; Eluent B—80% ACN in 0.1M TEAA; Gradient: Increase B (0-50%) in 20 min Dissolved in: CAN; Flow Rate: 1.5 ml/min 14. FIG. 11. 1H NMR analysis of 5'-DMT-N2-Fmoc deoxy guanosine. 500 MHz—DMSO/D2O 15. FIG. 12. Mass spectral analysis (positive ion analysis) of 5'-DMT-N2-Fmoc deoxy guanosine 16. FIG. 13. 31P NMR analysis of 5'-DMT-N6-Fmoc deoxy Adenosine-3'-CED phosphoramidite; solvent CDCL3.

Figure 14:
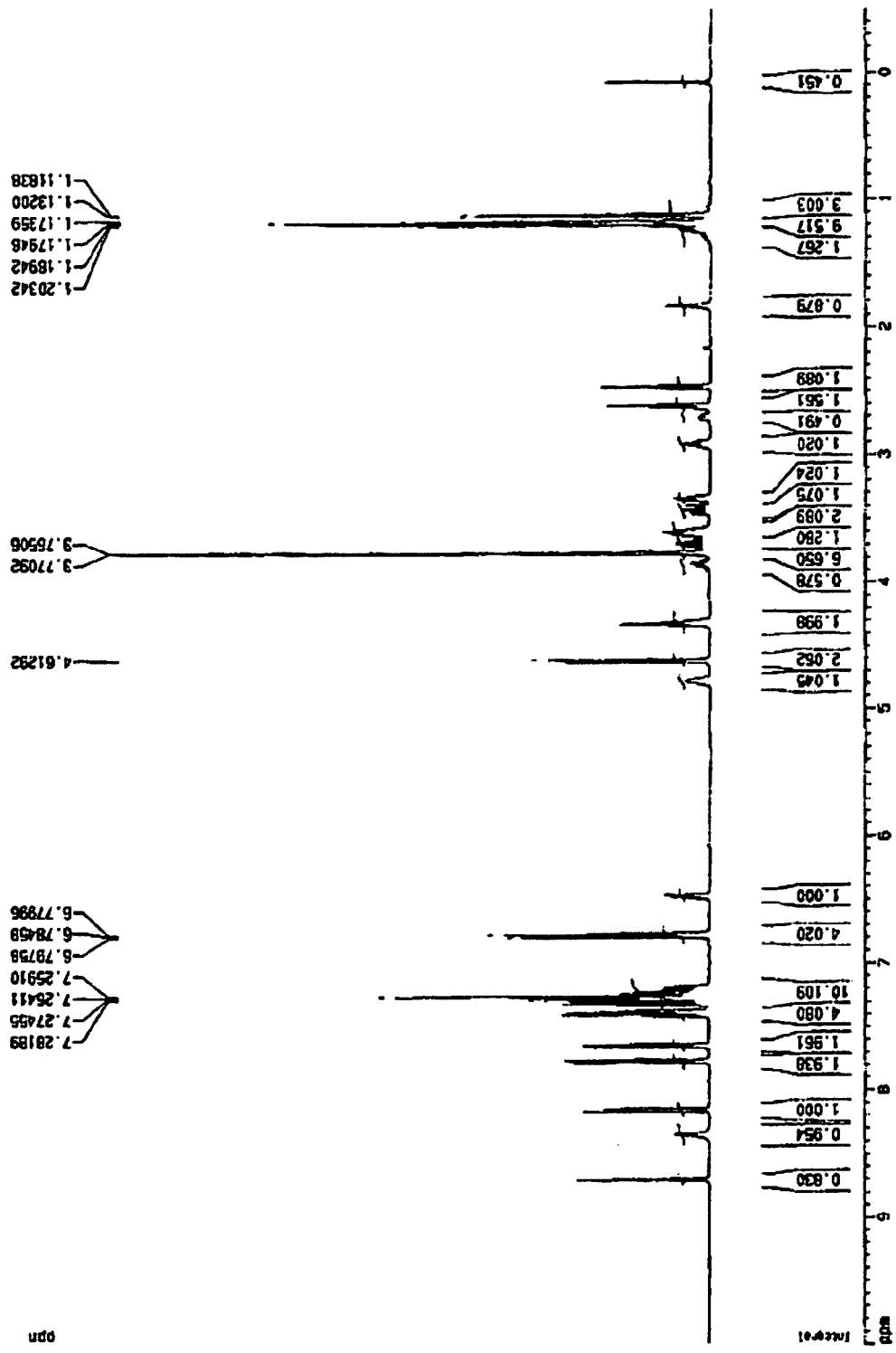

17. FIG. 14. 1H NMR analysis of 5'-DMT-N6-Fmoc deoxy Adenosine-3'-CED phosphoramidite; solvent CDCL3.

Figure 15:
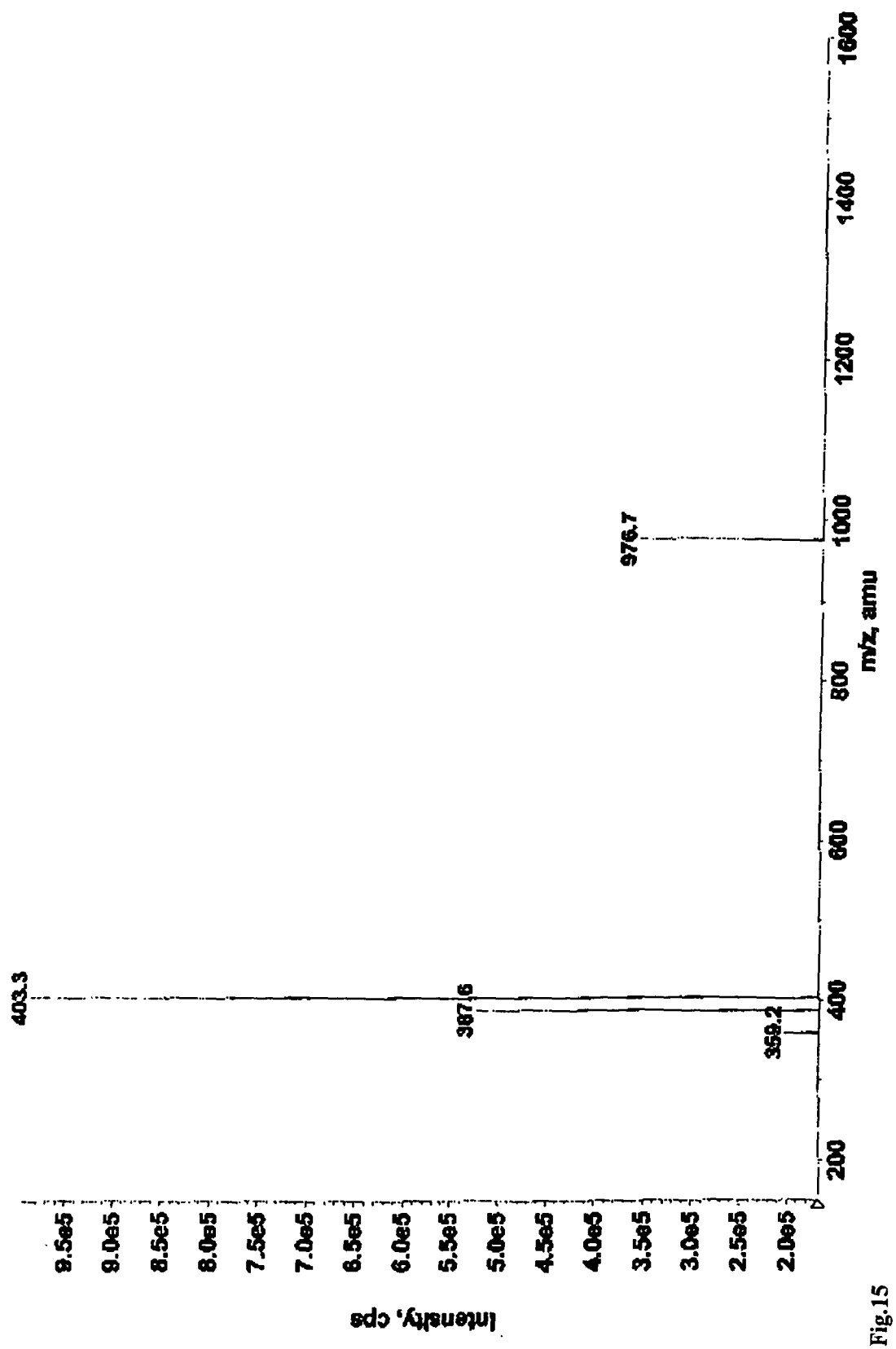
Figure 16:
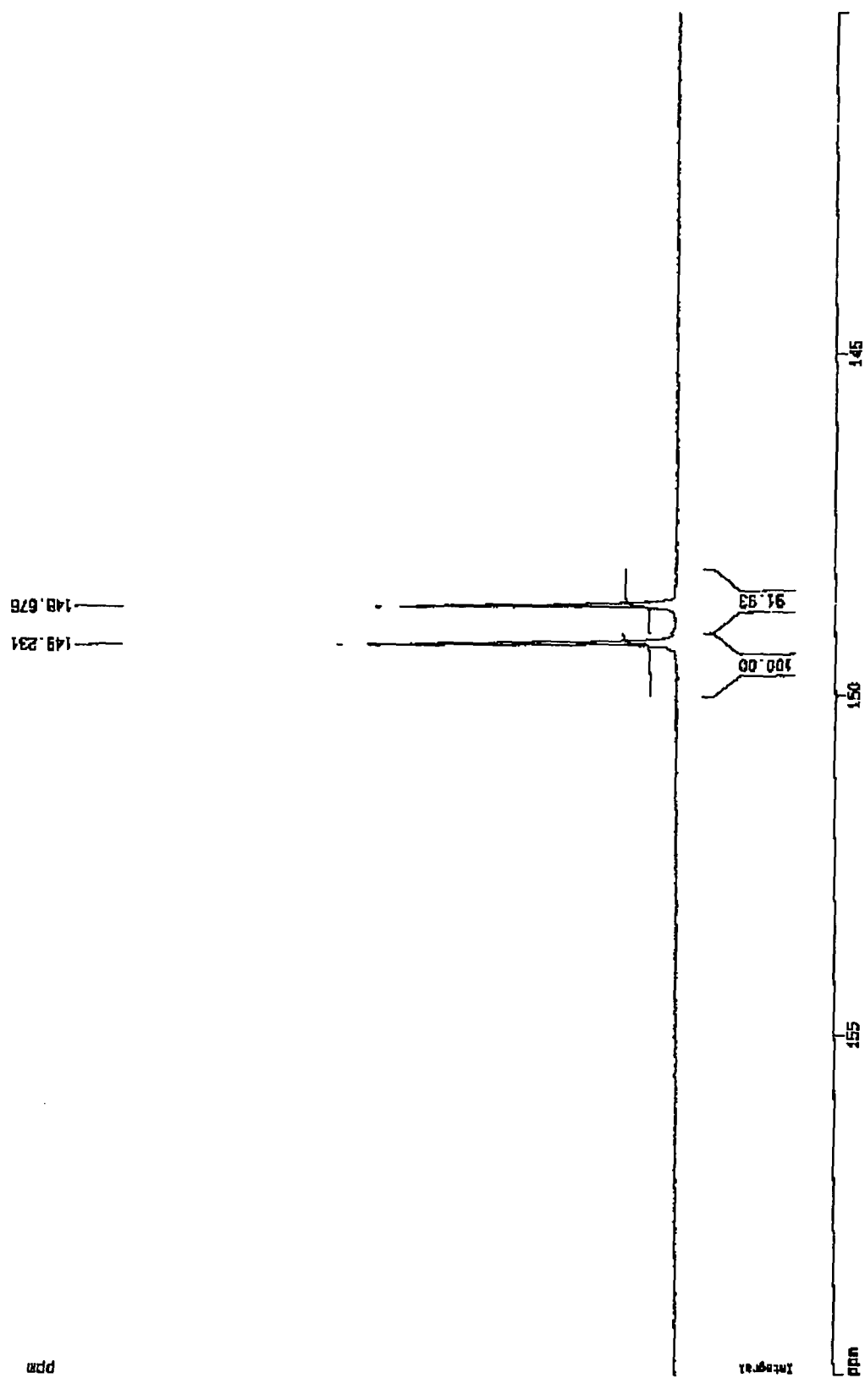

18. FIG. 15. Mass spectral analysis (positive ion analysis) of 5'-DMT-N6-Fmoc deoxy adenosine-3'-CED phosphoramidite 19. FIG. 16. 31P NMR analysis of 5'-DMT-N2-Fmoc deoxy guanosine-3'-CED phosphoramidite; solvent CDCL3.

Figure 17:
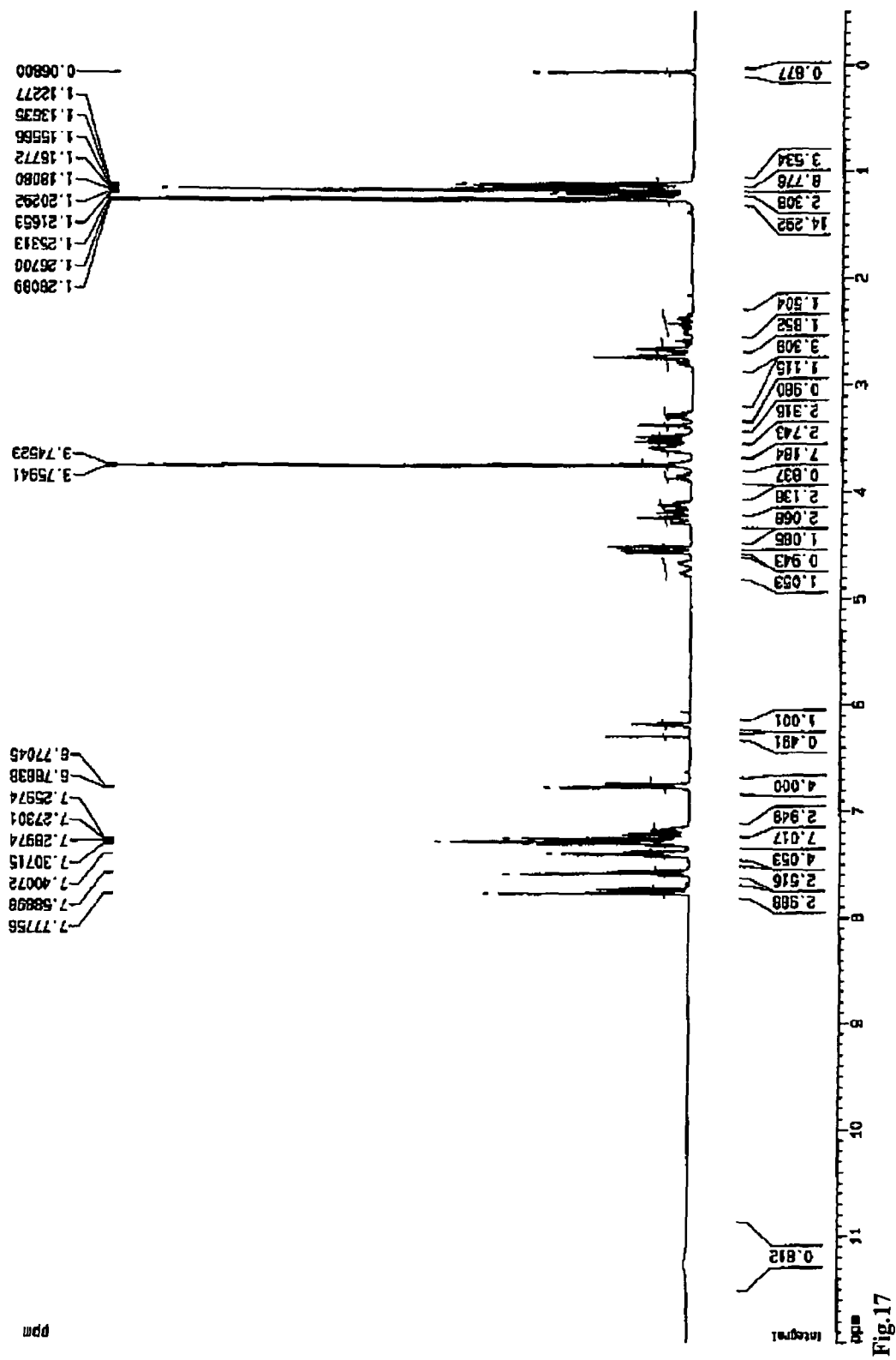

20. FIG. 17. 1H NMR of 5'-DMT-N2-Fmoc deoxy guanosine-3'-CED phosphoramidite; solvent CDCL3.

DETAILED DESCRIPTION OF THE INVENTION

The nucleic bases in our invention protected with 9-fluorenylmethyloxycarbonyl and sugar moiety in the nucleosides carry a 5'-DMT group in deoxyribonucleosides and 3'-cyanoethylphosphoramidite (CED) (Formula 3), 5'-DMT-3'-succinyl-Icaa CPG-N-Fmoc protected deoxy nucleosides (Formula 4) or 5'-DMT-2'-tBDsilyl (tBDSi)-3'-cyanoethylphosphoramidite (CED) (Formula 5).

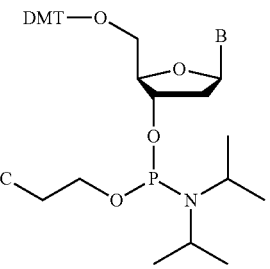

Where B = A (N-Fmoc), C (N-Fmoc), G (N-Fmoc),

Formula 3. 5'-DMT-N-Fmoc Protected Nucleoside-2' Deoxy-3'-Amidites

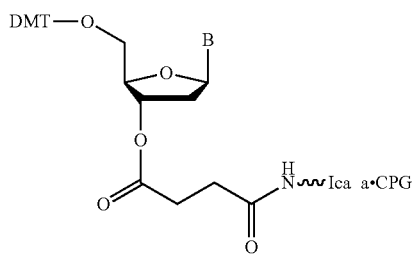

Where B = A (N-Fmoc), C (N-Fmoc), G (N-Fmoc).

Formula 4. 5'-DMT-N_FMOC Protected 2'-Deoxy Nucleoside-3'-Support

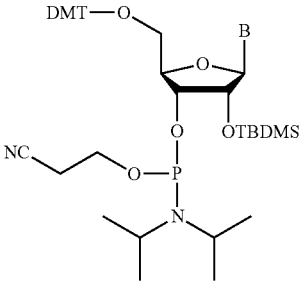

Where B = A (N-Fmoc), C (N-Fmoc), G (N-Fmoc),

Formula 5. 5'-DMT-2'-TBDMS-N-Fmoc Protected-Nucleoside-3'-Amidites

The invention also contemplates method for preparing the disclosed compositions. The starting base protection of the nucleoside (structure 23) affording N-Fmoc protected nucleoside (structure 24). Following tritylation reaction (with DMT-Chloride) of the nucleoside 24 with DMT chloride in pyridine gave desired nucleoside 25 in high yields for dA and dC. However in case of dG (structure 24, B$_2$; G) after DMT-Chloride reaction, there was almost 50% formation of an unknown product, which was carefully separated to obtain desired 5'-DMT-n-2-Fmoc-dG (structure 25; B$_2$; G(n-Fmoc) (Scheme 4).

Scheme 4:

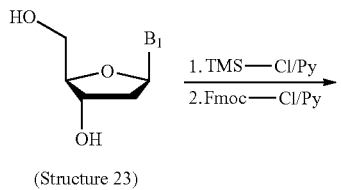

(Structure 23)

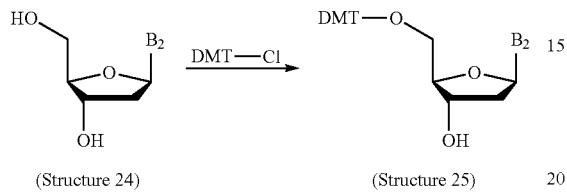

(Structure 24)   (Structure 25)

Where $B_1$ = a) A, b) C, c) G;
$B_2$ = a) A (N-Fmoc), b) C (N-Fmoc), c) G (N-Fmoc)

EXPERIMENTAL EXAMPLES

Example 1

Synthesis of $N^2$-Fmoc-5'-O-DMT-guanosine (25c) as Shown in the Scheme 4

FIGS. 9A, 9B, 10, 11, 12 are generated from the experimental data related to product 25c of this example.

$N^2$-Fmoc-Guanosine (24c):

To the solution of 30 g (112.3 mmol) of the compound of guanosine (1c) in 300 mL of pyridine were added 57.0 mL of trimethylsilyl chloride dropwise with stirring at 0-5° C. during the course of 30 min. After 1 hr the solution of 46 g (180 mmol) Fmoc-Cl in 100 mL of acetonitrile was added to the reaction mixture. The reaction mixture was stirred for 2.5 hrs at room temperature. The reaction mixture was cooled to 0° C. and quenched with 60 mL of cold water. Then reaction mixture was stirred for 5 min. Then 76.3 mL of conc. ammonium hydroxide were added to the reaction mixture with stirring for 2 min. Then solvent was removed under diminished pressure to ⅓ of the initial reaction mixture volume. The portion of 100 mL water was added to the reaction mixture and resulting solution was co-evaporated under diminished pressure to dryness. The residue was washed with 200 mL of ethyl ether, then 300 mL of chloroform was added to the residue and mixture was stirred for 2 hrs at room temperature. The solid product was filtered and washed with 200 mL of chloroform, then 100 ml of water and 100 mL of ethyl ether. The residual solvent was co-evaporated with 2×50 mL of acetonitrile. The final product 2c (24 g, 43.7%) was taken to the next step without further purification. TLC: $R_f$=0.4 chloroform/methanol—85:15.

$N^2$-Fmoc-5'-O-DMT-Guanosine (25c):

To the solution of 24 g (49.0 mmol) of the compound 2c in 240 mL of pyridine were added 22 g (64.9 mmol) of DMT-Cl by one portion at 0-5° C. with stirring. After 2 hrs the reaction mixture was quenched with 25 mL of methanol and ⅔ of solvent was removed under diminished pressure. Then residue was dissolved in 100 mL of chloroform and washed with 200 mL of conc. NaHCO₃ solution. Organic layer was washed with 200 mL brine. The organic layer was dried over Na₂SO₄. The solvent was removed under diminished pressure. Flash chromatography with 5:3:2:0.5 chloroform/hexanes/acetone/methanol provided 11 g (28.4%) of the compound 3c. ¹H NMR (d₆-DMSO/D₂O) ☐☐2.33 (ddd, 1H, J=6 Hz), J=12 Hz), 2.73 (ddd, 1H, J=6 Hz, J=12 Hz), 3.10 (br. d $J_{5a,5b}$=12 Hz), 3.55 (d. d, 1H, $J_{5a,5b}$=12 Hz, J=6.7 Hz) 3.68 (s, 6H), 3.96 (m, 1H), 4.33 (t, J=7.2 Hz) 4.43 (dd, 1H, J=4.9 Hz, J=10.5), 4.48 (d, 1H, J=7.2 Hz), 6.25 (t, 1H, J=6.3 Hz), 6.77 (dd, 4H, J=9 Hz, J=14.4 Hz), 7.22 (m, 7H), 7.32 (m, 4H), 7.42 (t, 2H, J=7.5 Hz), 7.79 (br. d, 2H, J=7.4 Hz) 7.88 (d, 2H, J=7.3 Hz) 8.06 (s, 1H), 8.25 (s, 1H). ESMS 814.8 [$C_{46}H_{41}N_5O_8$ (M+Na)⁺ requires 814.9].

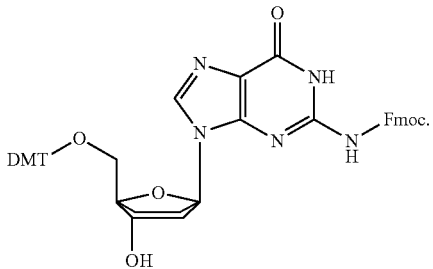

(structure 25 c).

Example 2

Synthesis of $N^4$-Fmoc-5'-O-DMT-Cytidine (25b)

FIGS. 5A, 5B, 6, 7, 8 are generated from the experimental data related to product 25b of this example.

$N^4$-Fmoc-Cytidine (24b):

Was prepared analogously to $N^2$-Fmoc-guanosine (24c). TLC: $R_f$=0.4 chloroform/methanol—85:15

$N^4$-Fmoc-5'-O-DMT-Cytidine (25b):

Was prepared analogously to $N^2$-Fmoc-5'-O-DMT-guanosine (25c). ¹H NMR (d₆-DMSO/D₂O) ☐☐☐☐☐☐☐☐ (m, 1H), 2.36-2.32 (m, 1H), 3.26-3.23 (m, 2H), 3.70 (s, 6H), 3.96-3.94 (br, 1H), 4.30-4.25 (br. m., 2H), 4.36-4.35 (br. d., 2H), 6.15 (dd, 1H), 6.80 (dd, 5H), 7.23-7.22 (13H), 7.7 (d, 2H), 7.9 (d, 2H), 8.1 (br. s, 1H). ESMS 774.7 (M+Na)⁺.

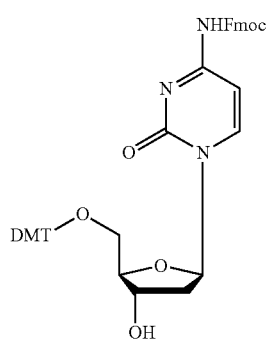

(Structure 25 b)

Example 3

Synthesis of N⁶-Fmoc-5'-O-DMT-Adenosine (25a)

N⁶-Fmoc-Adenosine (24a):
Was prepared analogously to N²-Fmoc-guanosine (24c). TLC: $R_f$=0.4 chloroform/methanol—85:15.

FIGS. 1A, 1B, 2, 3, 4 show experimental data related to product 25a of this example.

N⁶-Fmoc-5'-O-DMT-Adenosine (25a):
Was prepared analogously to N²-Fmoc-5'-O-DMT-guanosine (25c). ¹H NMR (d₆-DMSO/D₂O) □□2.43-2.38 (br, 1H), 2.97-2.92 (br. d, 1H), 3.19-3.17 (br. s, 21-1) 3.69-3.67 (two ss, 6H), 4.05-4.02 (m, 1H), 4.32-4.29 (br. t., 1H), 4.42-4.40 (d., 2H), 4.55-4.52 (m, 1H), 6.48 (dd, 11-1), 6.79-6.74 (four singles, 4H), 7.20-7.14 (m, 7H), 7.32-7.30 (m, 4H), 7.41-7.38 (t, 2H), 8.57 & 8.56 (two singlets, 2H). ESMS 776.8 and 798.8; M and (M+Na)⁺.

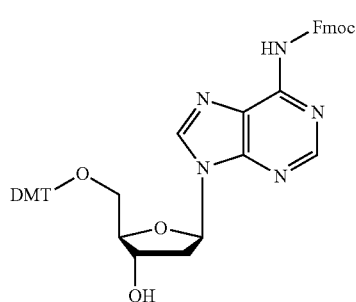

Structure 26 c

Example 4

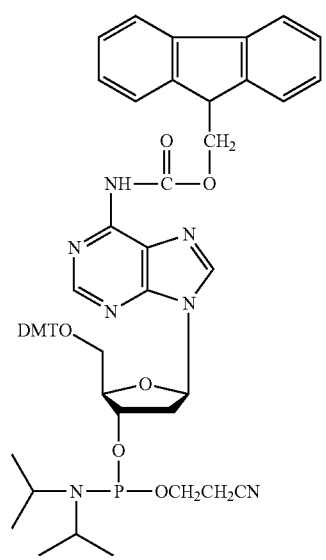

(Structure 7)

5'-DMT-N6-Fmoc-dA-p-cyanoethyl-phosphoramidite

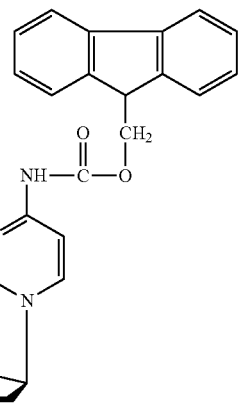

(Structure 8)

5'-DMT-N4-Fmoc-dC-p-cyanoethyl-phosphoramidite

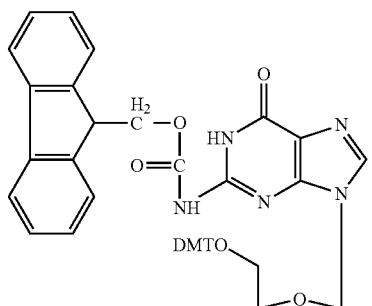

(Structure 9)

5'-DMT-N-2-FMOC-dG-p-cyanoethyl-phosphoramidite

Example 4

Synthesis of N-6-FMOC-5'-O-DMT-2'-Deoxy Adenosine-3'-Cyanoethyl Phosphoramidite (Structure 7)

To a solution of N-6-FMOC-5'-O-DMT-2'-deoxy Adenosine (0.5 g) in anhydrous acetonitrile (10 mL) was added diisopropyl ammonium tetrazolide (132 mg, 1.2 eq) at 0 C under argon atmosphere, followed by addition of n,n-diisopropyl cyanoethyl phosphorylating reagent (324 uL; 1.5 eq) under argon atmosphere at 0 C. The reaction mixture was sealed and stirred at room temperature for 1 hr. Work up was done by diluting in dichloromethane (50 mL), followed by washing with saturated bicarbonate (5 mL) previously cooled to 0 C, separating the organic layer and subsequently washing the organic layer with saturated brine solution. The organic layer was passed over anhydrous sodium sulfate. The organic layer was concentrated and the crude product was purified by short flash column chromatograph on Merck silica gel, 70-230 mesh, in Chloroform:acetone:triethylamine:90:8:2. The tlc of fractions was monitored in same solvent system and pure fractions combined and concentrated to yield foamy solid, yield 450 mg. $^1$H NMR (CDCl$_3$). The data is recorded in FIG. 14.

31P NMR (CDCl$_3$): Sharp doublet at 149.465 & 149.330 ppm, purity, 97%. FIG. 13 is generated from the experimental data related to this example.

ES/MS: Positive Ion mode: Observed Mass, 976.7; calculated 975.92. FIG. 15 is generated from the experimental data related to this example.

Example 5

Synthesis of N-2-FMOC-5'-O-DMT-2'-Deoxy Guanosine-3'-Cyanoethyl Phosphoramidite (Structure 9)

To a solution of N-2-FMOC-5'-O-DMT-2'-deoxy guanosine (0.5 g) in anhydrous acetonitrile (10 mL) was added diisopropyl ammonium tetrazolide (129 mg, 1.2 eq) at 0 C under argon atmosphere, followed by addition of n,n-diisopropyl cyanoethyl phosphorylating reagent (317 uL; 1.5 eq) under argon atmosphere at 0 C. The reaction mixture was sealed and stirred at room temperature for 1 hr. Work up was done by diluting in dichloromethane (50 mL), followed by washing with saturated bicarbonate (5 mL) previously cooled to 0 C, separating the organic layer and subsequently washing the organic layer with saturated brine solution. The organic layer was passed over anhydrous sodium sulfate. The organic layer was concentrated and the crude product was purified by short flash column chromatograph on Merck silica gel, 70-230 mesh, in Chloroform:acetone:triethylamine:80:18:2. The tlc of fractions was monitored in same solvent system and pure fractions combined and concentrated to yield foamy solid, yield 420 mg. $^1$H NMR (CDCl$_3$). The data recorded in FIG. 17.

31P NMR (CDCl$_3$): Sharp doublet at 149.231 & 148.676 ppm, clean peaks in amidite region. FIG. 16 is generated from the experimental data related to this example.

Notes on Claims

N1. Derivatized nucleoside and phosphoramidites of general formula 1.

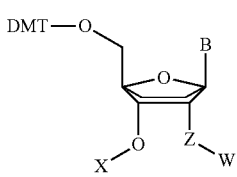

(Formula 1)

Where B=a) Adenine(N-Fmoc), b) Cytosine(N-Fmoc), c) Guanine(N-Fmoc), d) 5-methyl cytosine(N-Fmoc), e) 5-bromocytidine(N-Fmoc), i) 5-iodo cytosine(N-Fmoc), j) 5-fluorocytosine(N-Fmoc), k) 2,6-diaminopurine(N-Fmoc), l) 2-amino purine(N-Fmoc), Z=Oxygen & W is H; Z=Oxygen and W=tButyldimethyl silyl, TOM (triisopropyloxymethylene), acetal levulinyl ester (ALE), pivaloyloxy; cyanoethyl-methylene (CEM); dithiomethylene (DTM); Z=oxygen and W is methyl and other higher alkyls, alkenes and alkynes; Z=W=ribo Fluorine; Z=W=ara fluorine; Z=amino, W=amino protecting group; X=a) cyanoethyl-dialkyl phosphoramidite.
And; Where B=Z=W=H N2. Derivatized nucleoside and Solid Supports of general formula 2.

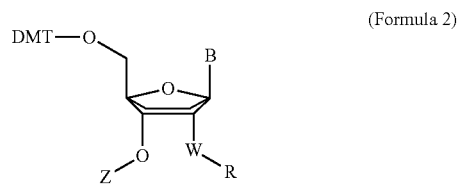

(Formula 2)

Where B=a) Adenine(N-Fmoc), b) Cytosine(N-Fmoc), c) Guanine(N-Fmoc), d) 5-methyl cytosine(N-Fmoc), e) 5-bromocytidine(N-Fmoc), i) 5-iodo cytosine(N-Fmoc), j) 5-fluorocytosine(N-Fmoc), k) 2,6-diaminopurine(N-Fmoc), l) 2-amino purine(N-Fmoc), Z is H; W=Oxygen and R=tButyldimethyl silyl, TOM (triisopropyloxymethylene), acetal levulinyl ester (ALE), pivaloyloxy; cyanoethylmethylene (CEM); dithiomethylene (DTM); Z=H and W=Oxygen and R=methyl and other higher alkyls, alkenes and alkynes; W=R=ribo Fluorine; W=R=ara fluorine; W=R=amino, W=R=amino protecting group; Z=a) succinimido long chain attached to a solid support, b) hydroquinione succinimido long chain spacer attached to solid support, c) oxalyl amido long chain spacer attached to solid support.
And; where Z=W=H N3. Derivatized nucleoside and solid supports of general formula 2.

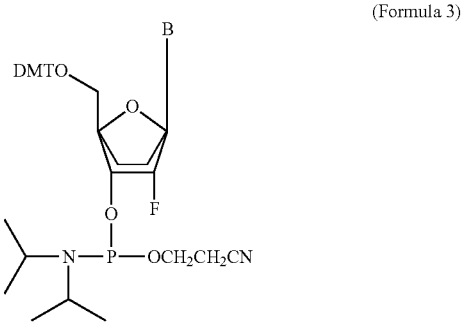

(Formula 3)

Where B=a) Adenine(N-Fmoc), b) Cytosine(N-Fmoc), c) Guanine(N-Fmoc), d) 5-methyl cytosine(N-Fmoc), e) 5-bromocytidine(N-Fmoc), i) 5-iodo cytosine(N-Fmoc), j) 5-fluorocytosine(N-Fmoc), k) 2,6-diaminopurine(N-Fmoc), l) 2-amino purine(N-Fmoc)

N4. Derivatized nucleoside and phosphoramidites of general formula 1.
 wherein
 Z is, sulfur or selenium; W is H N5. Derivatized nucleoside and solid supports of general formula 2.
 Wherein;
 Z is sulfur or selenium; W is H N6. A method for 3' to 5' direction of oligonucleotide bond formations shown in formula 4 in synthetic RNA oligomers. The RNA could consist of natural of modified nucleo bases as described in claim 1 to synthesize gapmers, phosphodiesters, phosphorothiates, phosphoselenate. The nucleoside compo-

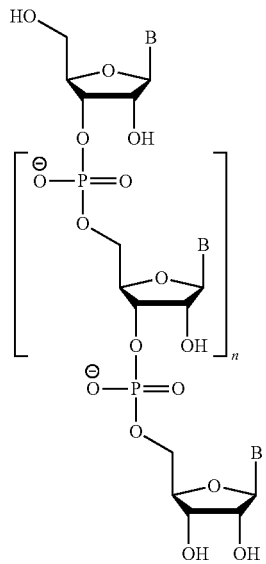

Formula 4

N7. A method for DNA & RNA synthesis using mild amine, secondary or tertiary amine for removal of N-Fmoc protecting group and cyanoethyl phosphate protecting group for RNA synthesis via 3' to 5' direction of oligonucleotide bond formations shown in formula 4 in synthetic RNA oligomers. The RNA could consist of natural of modified nucleo bases, gapmers, phosphodiesters, phosphorothiates, phosphoselenate. The nucleoside components will have N-Fmoc as protecting group. The synthesis could be performed on automated, semi automated DNA/RNA or other synthesizers or manually. The synthesis can be performed at various scales from microgram to kilogram scales.

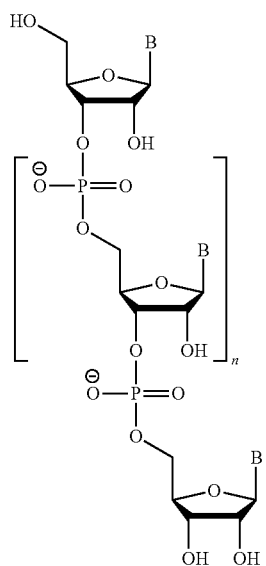

Formula 4

N8. A method for DNA & RNA synthesis using mild basic conditions, such as methyl amine solution, alkylamines, secondary or tertiary amine for removal of N-Fmoc protecting group and cyanoethyl phosphate protecting group for RNA synthesis via 3' to 5' direction of oligonucleotide bond formations shown in formula 4 in synthetic RNA oligomers. This is followed by wash of liberated protecting groups. The RNA could consist of natural of modified nucleo bases, gapmers, phosphodiesters, phosphorothiates, phosphoselenate. The nucleoside components will have N-Fmoc as protecting group. The synthesis could be performed on automated, semi automated DNA/RNA or other synthesizers or manually. The synthesis can be performed at various scales from microgram to kilogram scales.

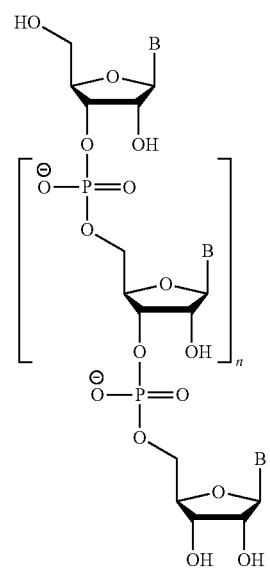

Formula 4

N9. A method for DNA & RNA synthesis using mild basic conditions, such as methyl amine solution, alkylamines, secondary or tertiary amine for removal of N-Fmoc protecting group and cyanoethyl phosphate protecting group for solid support attached DNA and RNA synthesis via 3' to 5' direction of oligonucleotide bond formations. This is followed by wash of liberated protecting groups. The support bound DNA and RNA could consist of natural of modified nucleo bases, gapmers, phosphodiesters, phosphorothiates, phosphoselenate. The nucleoside components during such oligo synthesis will have N-Fmoc as protecting group. The synthesis could be performed on automated, semi automated DNA/RNA or other synthesizers or manually. The synthesis can be performed at various scales from microgram to kilogram scales.

N10. The modified nucleosides incorporated by this method could consists of one or more of purine or pyrimidine modifications such as but not limited to, 5-Fluoro-U, 5-Fluoro dU, 5-fluoro-dC, 5-Fluoro-rC, pseudouridine, 5-methyl-dU, 5-methyl-rU, 5-methyl-dC, 5-methyl-rC, 5-bromo-dU, 5-bromo-rU, 5-bromo-dC, 5-bromo-rC, 5-iodo-dU, 5-iodo-rU, 5-vinyl-dU, 5-vinyl-rU, 5-vinyl thymidine, N-3 methyldeoxy uridine, N-3 methyl-ribouridine, N-3 methyl thymidine, 4-thio uridine, 4-thio-2'-deoxyuridine, 2,6-diaminopurine deoxy riboside, N-3 methyl ribothymidine, 2,6-diaminopurine riboside, 8-bromo 2'-deoxy adenosine, 8-bromo-r-adenosine, 8-oxo-deoxy adenosine, 8-oxo-riboadenosine, 8-oxo-2'-deoxy-adenosine, 8-oxo-riboadenosine, 8-oxo-deoxy inosine, 8-oxo-ribo inosine, 8-bromodeoxy inosine, 8-bromo-ribo-inosine, N-1 methyl-riboadenosine, N-1 methyl-2'-deoxy adenosine, N-1 methyl 2'-deoxy inosine, N-1 methyl riboadenosine, N-1 methyldeoxy guanosine, N-1-methyl-riboguanosine, etheno adenosine, etheno 2'-deoxy adenosine, purine 2'-deoxy riboside, purine-ribonucleoside, 2-aminopurine-2'-deoxyriboside, 2-aminopurine-ribonucleoside, N11. Labelling of internal positions of an RNA synthesized by this methods with chromophores such as, but not limited to Fluoroscein-C-5 dT, Dabcyl-C-5 thymidine, internal carboxyl group 5-dU-methylacrylate, biotin dT (biotin w attached via spacer to C-5 of dU), amino-dT (terminal amino attached via C-6 spacer to C-5 dU).

N12. The sugar modification of modified nucleosides could consist of 2'-deoxy-2'-fluoro ribo nucleosides (2'-F-ANAs) such as A, C, G, U, Inosine and modified nucleosides containing 2'-Fluoro, in one or more positions of an RNA or DNA sequence synthesized by this method.

N13. The sugar modification of modified nucleosides could consist of 2'-deoxy-2'-methoxy ribo nucleosides (2'-OMe-) such as A, C, G, U, Inosine and modified nucleosides containing 2'-methoxy, in one or more positions of an RNA or DNA sequence synthesized by this method.

N14. The sugar modification of modified nucleosides could consist of 2'-deoxy-2'-amino ribo nucleosides (2'-NH2) such as A, C, G, U, Inosine and modified nucleosides containing 2'-amino, in one or more positions of an RNA or DNA sequence synthesized by this method.

N15. The sugar modification of modified nucleosides could consist of 2'-deoxy-2'-terminal amino ribo nucleosides (2'-terminal NH2), attached via spacer from 2-10 atoms on nucleosides such as A, C, G, U, Inosine and modified nucleosides containing 2'-terminal amino, in one or more positions of an RNA or DNA sequence synthesized by this method.

N16. The sugar modification of modified nucleosides could consist of 2'-deoxy-2'-methoxy ethoxy ribo nucleosides (2'-MOE), such as A, C, G, U, Inosine and modified nucleosides containing 2'-MOE, in one or more positions of an RNA or DNA sequence synthesized by this method.

N17. The sugar modification of modified nucleosides could consist of other 2'-O-alkyl groups, such as 2'-deoxy-2'-ethoxy, propargyl, butyne ribo nucleosides (2'-OEt, O-Propargyl, 2'-O-Butyne), such as A, C, G, U, Inosine and modified nucleosides containing 2'-2'-OEt, O-Propargyl, 2'-O-Butyne, in one or more positions of an RNA or DNA sequence synthesized by this method.

N18. The sugar modification of modified nucleosides could consist of 2'-deoxy-2'-fluoro arabino nucleosides (2'-F-ANAs) such as A, C, G, U, Inosine and modified nucleosides containing 2'-F-ANAs), in one or more positions of an RNA or DNA sequence synthesized by this method.

N19. The sugar modification of modified nucleosides could consist of 2'-deoxy-2'-fluoro 4'-thioarabino nucleosides (4'-S-FANAs) such as A, C, G, U, Inosine and modified nucleosides containing 4'-S-FANAs in one or more positions of an RNA or DNA sequence synthesized by this method.

N20. The RNA comprising one or more 2'-5'-linkage within the sequence, at the 3'-end of the sequence or at the 5'-end of the sequence.

N21. The RNA having a 3'-end, synthesized by the method of this invention containing reverse attached deoxy nucleosides such as dT, dC, dG, thymidine, attached via their 3'-hydroxyl function.

N22. The RNA having a 3'-end synthesized by the method of this invention containing reverse attached ribonucleosides such as rA, rC, rG, rU, attached via their 2' or 3'-hydroxyl function.

N23. The RNA synthesis comprising 2'-triisopropylsilyloxy methyl (TOM), protecting group.

N24. The RNA synthesis comprising 2'-t-butyldithiomethyl (DTM) protecting group.

N25. The reverse RNA synthesis comprising the modified base comprising 2'-deoxy-2'-fluoro beta-D_arabinonucleic acid (FANA).

N26. The RNA synthesis comprising the modified base comprising 4'-thio-2'-deoxy-2'-fluoro beta-D_arabinonucleic acid (4'-Thio-FANA).

N27. The RNA synthesis comprising the modified sugar comprising 2'-OMethyl modification.

N28. The RNA synthesis comprising the modified sugar comprising Bicyclic locked nucleic acids (LNA's).

N29. The RNA synthesis comprising the modified sugar comprising altritol sugar modified oligonucleotides (ANA).

N30. The RNA synthesis comprising the step of conjugation of peptides, such as cell penetrating peptides (CPPs) or membrane permeant peptide (MPPs) utilizing either the free amine function of such peptides and a 3'-terminal carboxylic function on the reverse synthesized RNA. The CPPs and MPPs having an appropriate carboxyl function can be coupled to the free terminal amino function of an FMOC protected nucleotide or an oligonucleotide.

N31. The DNA and RNA synthesis comprising the 2'-5'-linked DNA units or 2'-5'-RNA units within the sequence, at the 3'-end of the sequence or at the 5'-end of the sequence.

We claim:
1. Derivatized ribonucleoside phosphoramidites of general Formula 1

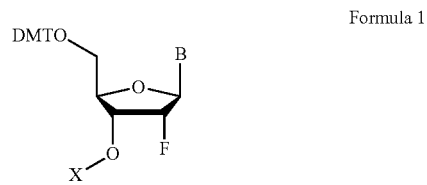

Formula 1 wherein,
B is selected from the group of protected nucleoside base radicals consisting of
9-($N^6$-FMOCadeninyl)-; 9-($N^6$-isopropyl phenoxyacetyladeninyl)-; 1-($N^4$-FMOCcytosinyl)-; 1-($N^4$-tert butylphenoxyacetylcytosinyl)-; 1-($N^4$-isopropylphenoxyacetylcytosinyl)-; 1-($N^4$-FMOC-5-methylcytosinyl)-; 1-($N^4$-FMOC-5-bromocytosinyl)-; 1-($N^4$-FMOC-5-iodocytosinyl)-; 1-($N^4$-FMOC-5-fluorocytosinyl)-; 9-($N^6$-FMOC-8-bromoadeninyl)-; 9-($N^6$-FMOC-8-oxoadeninyl)-; 9-($N^6$-FMOC-$N^1$-methyl adeninyl)-; 9-($N^2$-FMOC-$N^1$guanosinyl)-; 9-($N^2$,$N^6$-diFMOC-diaminopurinyl)-; 9-($N^2$-FMOC-amino purinyl)-; and F is a ribo fluoro substituent,
X is a phosphoramidite selected from the group consisting of cyanoethyl radical, alkyl radical and aryl radical;
DMT dimethoxytriphenyl is a protecting group.

2. Derivatized ribonucleoside Solid Supports of general Formula 2.

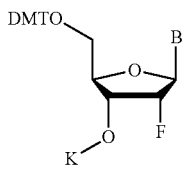

Formula 2 wherein,
B is selected from the group of protected nucleoside base radicals consisting of
9-($N^6$-FMOCadeninyl)-; 9-($N^6$-isopropyl phenoxyacetyladeninyl)-; 1-($N^4$-FMOCcytosinyl)-; 1-($N^4$-phenoxyacetylcytosinyl)-; 1-($N^4$-tert butylphenoxyacetylcytosinyl)-; 9-($N^2$-FMOCguanosinyl)-; 1-($N^4$-FMOC-5-methylcytosinyl)-; 1-($N^4$-FMOC-5-bromocytosinyl)-; 1-($N^4$-FMOC-5-iodocytosinyl)-; 1-($N^4$-FMOC-5-fluorocytosinyl)-; 9-($N^6$-FMOC-8-bromoadeninyl)-; 9-($N^6$-FMOC-8-oxoadeninyl)-; 9-($N^6$-FMOC-$N^1$-methyl adeninyl)-; 9-($N^2$-FMOC-$N^1$guanosinyl)-; 9-($N^2$,$N^6$-diFMOC-diaminopurinyl)-; 9-($N^2$FMOC-amino purinyl);

F is a ribo fluoro substituent,
K is selected from the group consisting of H, succinimido long chain attached to a long chain spacer solid support, hydroquinone succinimido long chain spacer attached to a solid support, and oxalyl amido long chain spacer attached to solid support; and
DMT dimethoxytriphenyl is a protecting group.

3. A process of oligonucleotide synthesis of length n, using solid support represented by formula (2),

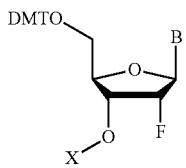

Formula 1

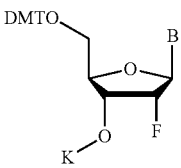

Formula 2 wherein,
n is an integer between 2 and 100;
B is selected from the group of protected nucleoside base radicals consisting of -9-($N^6$-FMOCadeninyl)-; 9-($N^6$-tert butyl phenoxyacetyladeninyl)-; 1-($N^4$-FMOCcytosinyl)-; 1-($N^4$-phenoxyacetylcytosinyl)-; 1-($N^4$-isopropyl phenoxyacetylcytosinyl)-; 9-($N^2$-FMOCguanosinyl)-; 1-($N^4$-FMOC-5-methylcytosinyl)-; 1-($N^4$-FMOC-5-bromocytosinyl)-; 1-($N^4$-FMOC-5-iodocytosinyl)-; 1-($N^4$-FMOC-5-fluorocytosinyl)-; 9-($N^6$-FMOC-8-bromoadeninyl)-; 9-($N^6$-FMOC-8-oxoadeninyl)-; 9-($N^6$-FMOC-$N^1$-methyl adeninyl)-; 9-($N^2$-FMOC-$N^1$guanosinyl)-; 9-($N^2$,$N^6$-diFMOC-diaminopurinyl)-; 9-($N^2$-FMOC-amino purinyl)-;
F is a ribo fluoro substituent,
X is a phosphoramidite selected from the group consisting of cyanoethyl radical, alkyl radical and aryl radical;
DMT dimethoxytriphenyl is a protecting group;
K is selected from the group consisting of H, succinimido long chain attached to a long chain spacer solid support, hydroquinone succinimido long chain spacer attached to a solid support, and oxalylamido long chain spacer attached to solid support; and
the process comprises the steps of:
(a) Taking a nucleoside attached to support represented by formula (2);
(b) Placing phosphoramidites represented by formula (1) in an oligonucleotide synthesizer;
(c) Performing oligonucleotide synthesis on said oligonucleotide synthesizer,
(d) Detaching synthesized oligonucleotide from the solid support;
(e) Removing the base protecting group from the oligonucleotide under mild basic conditions;
(f) Precipitating crude oligonucleotide.

* * * * *